(12) United States Patent
Edgren et al.

(10) Patent No.: US 8,524,277 B2
(45) Date of Patent: *Sep. 3, 2013

(54) EXTENDED RELEASE DOSAGE FORM

(75) Inventors: David E. Edgren, Los Altos, CA (US);
Patrick S.-L. Wong, Burlingame, CA (US); Gurdish K. Bhatti, Fremont, CA (US); Shu Li, Union City, CA (US); Robert R. Skluzacek, Newark, CA (US)

(73) Assignee: Alza Corporation, Vacaville, CA (US)

(*) Notice: Subject to any disclaimer, the term of this patent is extended or adjusted under 35 U.S.C. 154(b) by 1589 days.

This patent is subject to a terminal disclaimer.

(21) Appl. No.: 11/673,066

(22) Filed: Feb. 9, 2007

(65) Prior Publication Data
US 2007/0128279 A1   Jun. 7, 2007

Related U.S. Application Data

(63) Continuation of application No. 09/657,446, filed on Sep. 8, 2000, now abandoned, which is a continuation-in-part of application No. 09/249,700, filed on Feb. 12, 1999, now Pat. No. 6,245,357.

(60) Provisional application No. 60/077,133, filed on Mar. 6, 1998.

(51) Int. Cl.
*A61K 9/22* (2006.01)
*A61K 9/30* (2006.01)
*A61K 9/32* (2006.01)
*A01N 43/42* (2006.01)
*A01N 37/18* (2006.01)

(52) U.S. Cl.
USPC ........... 424/468; 424/475; 424/482; 514/282; 514/629

(58) Field of Classification Search
USPC .................. 424/468, 475, 482; 514/282, 629
See application file for complete search history.

(56) References Cited

U.S. PATENT DOCUMENTS

| | | | |
|---|---|---|---|
| 3,133,132 A | 5/1964 | Loeb et al. | |
| 3,173,876 A | 3/1965 | Zobrist | |
| 3,276,586 A | 10/1966 | Rosaen | |
| 3,541,005 A | 11/1970 | Strathmann et al. | |
| 3,541,006 A | 11/1970 | Bixler et al. | |
| 3,546,876 A | 12/1970 | Fokker et al. | |

(Continued)

FOREIGN PATENT DOCUMENTS

| | | |
|---|---|---|
| AR | 234 493 | 6/1987 |
| AR | 237 341 | 7/1988 |

(Continued)

OTHER PUBLICATIONS

XP002900470, Japan, Apr. 8, 1997, Morishita Roussel.

(Continued)

*Primary Examiner* — Blessing Fubara
(74) *Attorney, Agent, or Firm* — Samuel M. Kais

(57) ABSTRACT

A membrane system comprising an interior wall, a fluid-permeable exterior wall surrounding the interior wall and an internal compartment defined by the membrane system, wherein fluid permeability of the interior wall is responsive to osmolarity of an osmotic core within the internal compartment are disclosed. A controlled release dosage form comprising the membrane system and a process for delivering an osmotically active formulation from an osmotic pump over an extended period of time are also disclosed.

1 Claim, 5 Drawing Sheets

(56) References Cited

U.S. PATENT DOCUMENTS

| | | | |
|---|---|---|---|
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,014,334 | A | 3/1977 | Theeuwes et al. |
| 4,058,122 | A | 11/1977 | Theeuwes et al. |
| 4,063,064 | A | 12/1977 | Saunders et al. |
| 4,077,407 | A | 3/1978 | Theeuwes et al. |
| 4,088,864 | A | 5/1978 | Theeuwes et al. |
| 4,116,241 | A | 9/1978 | Theeuwes et al. |
| 4,160,020 | A | 7/1979 | Ayer et al. |
| 4,160,452 | A | 7/1979 | Theeuwes et al. |
| 4,200,098 | A | 4/1980 | Ayer et al. |
| 4,285,987 | A | 8/1981 | Ayer et al. |
| 4,327,725 | A | 5/1982 | Cortese et al. |
| 4,449,983 | A | 5/1984 | Cortese et al. |
| 4,569,937 | A | 2/1986 | Baker et al. |
| 4,576,604 | A | 3/1986 | Guittard et al. |
| 4,612,008 | A | 9/1986 | Wong et al. |
| 4,662,880 | A | 5/1987 | Hamel et al. |
| 4,705,039 | A | 11/1987 | Sakaguchi et al. |
| 4,713,248 | A | 12/1987 | Kjorneas et al. |
| 4,716,041 | A | 12/1987 | Kjornaes et al. |
| 4,743,248 | A | 5/1988 | Bartoo et al. |
| 4,783,337 | A | 11/1988 | Wong et al. |
| 4,786,503 | A | 11/1988 | Edgren et al. |
| 4,798,725 | A * | 1/1989 | Patel .................. 424/456 |
| 4,814,183 | A | 3/1989 | Zentner et al. |
| 4,820,522 | A | 4/1989 | Radebaugh et al. |
| 4,863,456 | A | 9/1989 | Stephen et al. |
| 4,892,739 | A | 1/1990 | Shah et al. |
| 4,902,514 | A | 2/1990 | Barclay et al. |
| 5,082,668 | A | 1/1992 | Wong et al. |
| 5,160,744 | A | 11/1992 | Jao et al. |
| 5,202,128 | A | 4/1993 | Morella et al. |
| 5,273,760 | A | 12/1993 | Oshlack et al. |
| 5,378,474 | A | 1/1995 | Morella et al. |
| 5,472,712 | A | 12/1995 | Oshlack et al. |
| 5,472,742 | A | 12/1995 | Lee et al. |
| 5,478,577 | A | 12/1995 | Sackler et al. |
| 5,500,227 | A | 3/1996 | Oshlack et al. |
| 5,558,879 | A | 9/1996 | Chen et al. |
| 5,656,295 | A | 8/1997 | Oshlack et al. |
| 5,660,861 | A | 8/1997 | Jao et al. |
| 5,667,005 | A | 9/1997 | Kakutani et al. |
| 5,667,805 | A | 9/1997 | Merrill et al. |
| 5,702,725 | A | 12/1997 | Merrill et al. |
| 5,840,731 | A * | 11/1998 | Mayer et al. .................. 514/289 |
| 5,853,558 | A | 12/1998 | Gray et al. |
| 5,856,558 | A | 1/1999 | Pasenok et al. |
| 5,863,558 | A | 1/1999 | Jao et al. |
| 5,869,098 | A * | 2/1999 | Misra et al. .................. 424/484 |
| 5,914,129 | A * | 6/1999 | Mauskop .................. 424/464 |
| 5,914,131 | A | 6/1999 | Merrill et al. |
| 5,916,595 | A | 6/1999 | Chen et al. |
| 5,958,458 | A * | 9/1999 | Norling et al. .................. 424/490 |
| 6,245,357 | B1 * | 6/2001 | Edgren et al. .................. 424/473 |

FOREIGN PATENT DOCUMENTS

| | | |
|---|---|---|
| AR | 254 392 | 7/2000 |
| AR | 254 640 | 11/2000 |
| AR | 255 653 | 7/2002 |
| EP | 0068838 | 1/1983 |
| EP | 0621032 | 10/1994 |
| EP | 636 370 A1 | 2/1995 |
| EP | 0 0649 657 | 4/1995 |
| EP | 00649657 A | 4/1995 |
| EP | 0 793 959 A1 | 9/1997 |
| EP | 144 2745 A1 | 8/2004 |
| JP | A 9 87203 | 6/1975 |
| JP | A 4 74137 | 3/1992 |
| JP | A5 500222 | 1/1993 |
| JP | A 7 2648 | 12/1993 |
| JP | A6 500774 | 1/1994 |
| JP | A7 252140 | 10/1994 |
| JP | A9295933 | 11/1994 |
| JP | A7-089849 | 4/1995 |
| JP | 7 165609 | 6/1995 |
| JP | 7 206679 | 8/1995 |
| JP | A 9 509184 | 9/1997 |
| WO | WO85/03436 | 8/1985 |
| WO | WO 91 03247 A1 | 3/1991 |
| WO | WO 92 04011 A1 | 3/1992 |
| WO | WO 92 04012 A1 | 3/1992 |
| WO | WO 95 22962 A1 | 8/1995 |
| WO | WO 96 14058 | 5/1996 |
| WO | WO 96 14058 A1 | 5/1996 |
| WO | WO 97 04780 A1 | 2/1997 |
| WO | WO 98 05314 A1 | 2/1998 |
| WO | WO 99 29297 | 6/1999 |

OTHER PUBLICATIONS

Handbook of Common Polymers, Scott J. R. and Roff, W. J., 1971, CRC Press, Cleveland, OH.
Modern Plastics Encyclopedia, vol. 46, pp. 62-70 (1969).
Pharmaceutical Sciences, Remington, 14th Ed., pp. 1626-1648 (1970), Mack Publishing Co., Easton, PA.
Santus et al "Osmotic Drug Delivery: A Review of the Patent Literature" J of Controlled Releases 1995 vol. 35 pp. 1-21.
HYDROCET® Capsules (Hydrocodone Bitartrate and Acetaminophen Capsules) Label Carnrick Laboratories Inc. Physician's Desk Reference 1998 pp. 824-825.
LORTAB—Hydrocodone Bitartrate and Acetaminophen Tablet Label UCB Pharma, Inc. Rev. 4E Jan. 2008.
LORCET®-HD Label Forest Pharmceuticals Physician's Desk Reference 1998 pp. 951-952.
MS CONTIN—Morphine Sulfate Tablet, Film Coated, Extended Release Label Purdue Pharma LP 2009.
NORCO—Hydrocodone Bitartrate and Acetaminophen Tablet Label Keltman Pharmaceuticals Inc.Revision 4.
ORAMORPH SR—Morphine Sulfate Tablet Label Xanodyne Pharmaceuticals, Inc Rev. Feb. 2006.
Perrigo Ibuprofen—Ibuprofen Tablet Label Perrigo Pharmaceuticals Company Revised: Dec. 2009.
Procardia XL—Nifedipine Tablet, Film Coated, Extended Release Label Pfizer Laboratories Div Pfizer Inc Aug. 2010.
Tylenol Label McNeil Consumer Healthcare Div McNeil-PPC, Inc Rev Nov. 2009.
Kadian Label Actavis Kadian LLC Rev Feb. 2009.
Allay Ivax Pharms Approval Date Jan. 13, 1989 FDA Orange Book http://www.accessdata.fda.gov/scripts/oder/ob/docs/obdetail.cfm?Appl_No=0899078,1=OB_Disc Accessed Nov. 1, 2011.
Anexsia Mallinckrodt Approval Date Apr. 23, 1987 FDA Orange Book http://www.accessdata.fda.gov/scripts/oder/ob/docs/obdetail.cfm?Appl_No=089160&TABLE1=OB_Rx Accessed Nov. 1, 2011.
Anexsia 7.6/650 Mallinckrodt Approval Date Sep. 30, 1987 FDA Orange Book http://www.accessdata.fda.gov/scripts/cder/ob/docs/obdetail.cfm?Appl_No=089725&TABLE1=OB_Rx Accessed Nov. 2, 2011.
Azdone Schwarz Pharma Approval Date Jan. 25, 1988 FDA Orange Book http://accessdata.fda.gov/scripts/cder/ob/docs/obdetail.cfm?Appl_No=089420&TABLE1=OB_Disc Accessed Nov. 1, 2011.
Co-Gesic 500MG 5MG UCB Inc Approval Date May 3, 1982 FDA Orange Book http://www.accessdata.fda.gov/scripts/oder/ob/docs/obdetail.cfm?Appl_No=087757&TABLE1=OB_Rx Accessed Nov. 1, 2011.
Kadian 20MG, 50MG, 100MG Actatis Elizabeth Approval Date Jul. 3, 1996 FDA Orange Book http://www.accessdata.fda.gov/scripts/cder/ob/docs/obdetail.cfm?Appl_No=020616&TABLE1=OB_Rx Accessed Nov. 2, 2011.
Lorcet-HD 500MG 5MG Mallinckrodt Approval Date Jul. 8, 1982 FDA Orange Book http://www.accessdata.fda.gov/scripts/oder/ob/docs/obdetail.cfm?Appl_No=087336&TABLE1=OB_Disc Accessed Nov. 2, 2011.
Lortab 500MG, 10MG UCB Inc Approval Date Jan. 26, 1996 FDA Orange Book http://www.accessdata.fda.gov/scripts/oder/ob/docs/obdetail.cfm?Appl_No=040100&TABLE1=OB_Rx Accesssed Nov. 2, 2011.

Lortab500MG, 5MG UCB Inc Approval Date Jul. 9, 1982 FDA Orange Book http://www.accessdata.fda.gov/scripts/cder/ob/docs/obdetail.cfm?Appl_No=087722&TABLE1=OB_Rx Accessed Nov. 2, 2011.

MS Contin 30MG Purdue Pharma LP Approval Date May 29, 1987, MS Contin 60MG Purdue Pharma LP Approval Date Apr. 8, 1988, MS Contin 15MG Purdue Pharma Lpapproval Date Sep. 12, 1989 MS Contin 100MG Purdue Pharma LP Approval Date Jan. 16, 1990, MS Contin 200MG Purdue Pharma LP Approval Date Nov. 8, 1993 FDA Orange Book http://www.accessdata.fda.gov/scripts/cder/ob/docs/obdetail.cfm?Appl_No=019516&TABLE1=OB_Rx Accessed Nov. 1, 2011.

Norco 325MG,10MG Watson Labs Approval Date Feb. 14, 1997, Norco 325MG;7.5 MG Watson Labs Approval Date Sep. 12, 2000 FDA Orange Book http://www.accessdata.fda.gov/scripts/cder/ob/docs/obdetail.cfm?Appl_No=040148&TABLE1=OB Rx Accessed Nov. 2, 2011.

Norco 325MG 5MG Watson Labs Approval Date Jun. 25, 1997 FDA Orange Book http://www.accessdata.fda.gov/scripts/oder/ob/docs/obdetail.cfm?Appl_No=040099&TABLE1=OB_Rx Accessed Nov. 2, 2011.

Oramorph SR 30MG Xanodyne Pharm Approval Date Aug. 15, 1991, Oramorph SR 60MG Xanodyne Pharm Approval Date Aug. 15, 1991, Oramorph SR 100MG Xanodyne Pharm Approval Date Aug. 15, 1991, Oramorph SR 15MG Xanodyne Pharm Approval Date Nov. 23, 1994 FDA Orange Book http://www.accessdatafda.gov/scripts/cder/ob/docs/obdetail.cfm?Appl_No=019977TABLE1=OB_Rx Accessed Nov. 1, 2011.

Procardia XL 30MG, 60MG, 90MG. Pfizer Approval Date Sep. 6, 1989 FDA Orange Book http://www.aceessdata.fda.gov/scripts/cder/ob/docs/obdetail.cfm?Appl_No=019684&TABLE1=OB_Rx Accessed Nov. 2, 2011.

Tylenol W Codeine No. 3 300MG, 30MG Janssen Pharms Approval Date Prior to Jan. 1, 1982;Tylenol W Codeine No. 4 300MG, 60MG Janssen Pharms Approval Date Prior to Jan. 1, 1982 FDA Orange Book http://www.accessdata.fda.gov/scripts/cder/ob/docs/obdetail.cfm?Appl_No=085055&TABLE1=OB_Rx Accessed Nov. 1, 2011.

Vicodin 500MG 5MG Abbott Approval Date Jan. 7, 1983 FDA Orange Book http://www.accessdata.fda.gov/scripts/cder/ob/docs/obdetail.cfm?Appl_No=088058&TABLE1=OB_Rx Accessed Nov. 1, 2011.

Vicodin HP 660MG, 10MG Abbott Approval Date Sep. 23, 1996 FDA Orange Book http://www.accessdata.fda.gov/scripts/cder/ob/docs/obdetail.cfm?Appl_No=040117&TABLE=OB_Rx Accessed Nov. 1, 2011.

Vicodin ES 750MG, 7.5MG Abbott Approval Date Dec. 9, 1988 FDA Orange Book http://accessdata.fda.gov/scripts/cder/ob/docs/obdetail.cfm?Appl_No=089736&TABLE1=OB_Rx Accessed Nov. 1, 2011.

Vicoprofen 7.5MG, 200MG Abbott Approval Date Sep. 23, 1997 FDA Orange Book http://www.aceessdata.fda.gov/scripts/cder/ob/docs/obdetail.cfm?Appl_No=020716&TABLE1=OB_Rx Accessed Nov. 1, 2011.

Acetaminophen Tablet, Extended Release, Oral Perrigo Approval Date Feb. 25, 2000 FDA Orange Book http://www.accessdata.fda.gov/scripts/cder/ob/docs/obdetail.cfm?Appl_No=075077 &TABLE1=OB_OTC Accessed Mar. 1, 2012.

Hydrocet Acetaminophen Hydrocodone Bitartrate Capsule, Oral, Hydrocodone Bitartrate and Acetaminophen Mallinckrodt/Carnrick 500MG, 5MG Approval Date Aug. 9, 1985 FDA Orange Book http://www.accessdata.fda.gov/scripts/cder/ob/docs/obdetail.cfm?Appl_No=089006&TABLE1=OB_Disc, Accessed Mar. 1, 2012.

* cited by examiner

EXTENDED RELEASE DOSAGE FORM

CROSS-REFERENCE TO RELATED APPLICATIONS

This application is a continuation of patent application U.S. Ser. No. 09/657446, which claims benefit of international application PCT/US99/04192, filed on Feb. 26, 1999 and is a continuation-in-part of patent application U.S. Ser. No. 09/249,700, filed on Feb. 12, 1999, now U.S. Pat. No. 6,245,357, which applications in turn claim priority from provisional application U.S. Ser. No. 60/077,133, filed Mar. 6, 1998. The content of these applications are incorporated herein by reference.

FIELD OF THE INVENTION

This invention pertains to both a novel and therapeutically useful dosage form. In particular, the invention relates to a dosage form that administers a dose of a therapeutic agent in an extended and linear-release profile for an indicated therapy. Specifically, the invention concerns a membrane system comprising an internal compartment surrounded by an interior and an external wall, wherein the fluid permeability of the interior wall is responsive to osmolarity of an osmotic core comprised in the internal compartment. The invention concerns also a method of administering the dosage form to provide a dose of drug for therapy.

BACKGROUND OF THE INVENTION

To improve the effectiveness of drug therapy and to reduce possible systematic side effects, many attempts have been made to deliver drugs in a controlled profile to human patients. The advantage of controlled release dosage forms are well-known in both the pharmaceutical and medical sciences. The therapeutical benefits of controlled-release dosage forms include the pharmacokinetic ability to maintain a pre-planned blood level of an administered drug over a comparatively longer period of time. The therapeutical benefits include also a simultaneous increase in patient compliance and a reduction in the number of doses of drug administered to a patient.

The prior art made available controlled release dosage that sought to provide a drug release rate profile that matched the blood physiological and chrono-pharmacological requirements needed for therapy. For example, U.S. Pat. Nos. 3,845,770 and 3,916,899 issued to Theeuwes and Higuchi pertains to an osmotic dosage form for delivering various drugs to a patient environment of use. The dosage forms disclosed in these patents are manufactured comprising a wall that surrounds a compartment comprising a drug with an exit in the wall for delivering the drug to a patient. In U.S. Pat. Nos. 4,008,719; 4,014,334; 4,058,122; 4,116,241; and 4,160,452 patentees Theeuwes and Ayer made available dosage forms comprising an inside and an outside wall made of poly(cellulose acylate) for delivering a dosage of drug to a patient in need thereof.

The history of the prior art dosage forms indicates a serious need exists for a novel and useful dosage form that provides an unexpected advancement in the science of dosage forms. For example, the prior art dosage forms lack the present ability to mask an unpleasant taste, they did not maintain the stability of a drug formulation, and the dosage forms did not protect a drug from oxidation. Then too, the drug formulation in the dosage form permitted the drug release profile to decline over time, thereby administering a nontherapeutic dose of drug. The wall of the dosage forms exposed to the gastrointestinal tract were lipophilic, they absorbed endogenous fats and consequently evidenced a decrease in structural integrity as seen in flaws or cracks in the wall. Moreover, the dosage forms wall and its drug formulation did not act in concert for providing a controlled linear drug delivery profile over an extended time. Likewise, prior art dosage forms were formulated with water-leachable components within the membrane to control delivery rate of drug which water-leachable components diffused from the membrane against the direction of osmotic water flux making reproducibility and control of delivery rate patterns difficult, as seen in U.S. Pat. No. 5,160,744.

It is clear from the above presentation that a long-felt need exists for a dosage form comprising a walled structure and a drug formulation that function together for administering orally a drug at a controlled and sustained-release drug delivery profile with time. The need exists for a dosage form for administering a drug in a linear profile for treating infectious diseases, respiratory diseases, the cardiovascular system, blood and spleen, the digestive system, metabolic disorders, the endocrine system, the urogenital tract, sexually transmitted diseases, the nervous system, the locomotor system, psychiatric disorders and for providing symptomatic care. A dosage form is needed for replacing immediate-release dose-dumping forms administered three or four times daily. There are serious reasons for seeking a dosage form that replaces immediate-release forms, including a means for reducing peak-blood levels followed by a sharp drop in blood levels, a means for lessening side effects, a means for manufacturing the structural integrity of the dosage form, and a means for reducing the number of solvents used to manufacture the dosage form.

OBJECTS OF THE INVENTION

Accordingly, in view of the above presentation, it is an immediate object of this invention to provide both a novel and a useful dosage form that overcomes the disadvantages associated with the prior art.

Another object of the present invention is to satisfy a long-felt need by providing a dosage form for controlled delivery wherein a therapeutic agent is administered in a linear profile over an extended period of time for an indicated therapy.

In one embodiment the invention provides a membrane system comprising an interior wall surrounding an internal compartment, wherein fluid permeability of the interior wall is responsive to osmolarity of an osmotic core comprised in the internal compartment; and a fluid-permeable exterior wall surrounding the interior wall, wherein the interior wall and the exterior wall are in contacting relationship. The walls of the membrane system maintain its physical and chemical integrity during the administration of a drug. Additionally, the exterior wall provides a bioprotective wall that shields the dosage form from injury and/or destruction in a gastrointestinal environment.

In preferred embodiments, the interior wall comprises hydrophobic and hydrophilic substance, wherein the hydrophilic substance exhibits an aqueous solubility responsive to osmotic pressure and/or ionic strength of the osmotic core. In an alternative embodiment, the interior wall comprises a polymer composition, wherein the hydrophilic substance exhibits an aqueous solubility responsive to degree of hydration of the polymer composition.

Another object of this invention is to provide a membrane system wherein the inside wall comprises a hydrophobic polymer insoluble in the digestive system and hydrophilic polymer soluble in the digestive system wherein the hydrophilic polymer enhances the fluid flux of the interior wall.

In preferred embodiments, the inner wall comprises a member selected from the group consisting of hydrogel polymers, osmopolymers, osmotically-effective compounds, suspending agents, compounds for forming passageway, pore formers polypeptides, proteins, polysaccharides, cellulose derivatives, surfactants, synthetic polymers and inorganic polymers. More preferably, the membrane system comprises a hydrophobic substance comprising ethyl acetate or cellulose acetate; a hydrophobic membrane comprising hydroxyalkylcellulose; and a semipermeable substance comprising cellulose acetate.

The internal compartment membrane system comprises a therapeutic agent. In additional embodiments, the internal compartment further comprises a pharmaceutically acceptable osmotically-effective compound and optionally a pharmaceutically acceptable hydrogel polymer. In alternative embodiments, internal compartment further comprises an expandable layer, wherein the expandable layer comprises an osmotically-effective compound.

Another object of the invention is to provide a controlled release dosage form comprising an osmotic core; an interior wall surrounding the osmotic core, wherein fluid permeability of the interior wall is responsive to osmolarity of the osmotic core; and a fluid-permeable exterior wall surrounding the interior wall.

Another object of the invention is to provide a controlled release dosage form comprising an osmotic core; an interior wall in contact with the osmotic core, wherein fluid permeability of the interior wall is responsive to osmolarity of said osmotic core; and a fluid-permeable exterior wall in contact with the interior wall.

The osmotic core comprises a therapeutic agent; and further the osmotic core, the internal wall and the external wall act in concert to provide a controlled delivery of the therapeutic agent over an extended or sustained-release period of time, preferably over a period of about 30 minutes to about 30 hours, more preferably about 6 hours to about 24 hours, and even more preferably about 4 hours to about 24 hours. The interior wall, the exterior wall and the osmotic core are as described in the membrane system above.

Another object of the invention is to provide a transport mechanism whereby water-soluble flux enhancers within the interior wall, during the operation of the dosage form, are transported by diffusion from the interior wall in the same direction as the osmotic water-flow passing through the membrane system.

Another objective of the invention is to provide a controlled release dosage form, wherein said inner wall comprises a member selected from the group consisting of hydrogel polymers, osmopolymers, osmotically-effective compounds, suspending agents, compounds for forming passageway, pore formers polypeptides, proteins, polysaccharides, cellulose derivatives, surfactants, synthetic polymers and inorganic polymers. In a preferred embodiment, the controlled release dosage form comprises a hydrophobic substance comprising ethyl acetate or cellulose acetate; a hydrophobic membrane comprising hydroxyalkylcellulose; and a semipermeable substance comprising cellulose acetate.

Another object of the invention is to provide a process for delivering an osmotically active formulation from an osmotic pump over an extended period of time comprising: (i) disposing the formulation in an osmotic pump; (ii) exposing the osmotic pump to a fluid environment to cause delivery of the formulation therefrom in response to osmotic imbibition of fluid into the pump; and (iii) increasing the fluid permeability of the pump in response to decreasing osmolarity of the formulation.

The formulation comprises a therapeutic agent, wherein the therapeutic agent is delivered in an extended-linear, non-declining release profile over an extended or sustained-release period of time, preferably over a period of about 30 minutes to about 30 hours, more preferably about 6 hours to about 24 hours, and even more preferably about 4 hours to about 24 hours. The sustained release rate provided by the invention is free from changes induced by the environment of the gastrointestinal tract. In a preferred embodiment, the extended-linear release profile is a zero order release profile. In an alternative embodiment, the extended-linear release profile is an ascending release profile.

Another objective of the invention is to provide a membrane comprising a semipermeable membrane having a control membrane disposed thereon, the water permeability of the control membrane being responsive to changes in the osmolarity of fluid contacting said control membrane. The composition of the control member corresponds to the composition of the interior wall as described above. The composition of the semipermeable membrane corresponds to the composition of the exterior wall as described in the membrane system above.

Another objective of the invention is to provide an osmotic pump comprising: an osmotic core; a semipermeable membrane enclosing at a least a portion of the core; and a control membrane disposed between at least a portion of the semipermeable membrane and the core, the water permeability of the control membrane being responsive to changes in the osmolarity of the core.

Another object of the present invention is to provide a dosage form manufactured as an osmotic drug delivery device by standard manufacturing procedures into sizes, shapes and structures that represent an advancement in the drug delivery art.

Another object of the invention is to provide a method for treating a patient with a medication administered from a controlled-release dosage form.

Other objects, features, aspects, and advantages of the invention will be more apparent to those versed in the drug dispensing art from the following detailed specification taken in conjunction with the Figures and the accompanying claims.

BRIEF DESCRIPTION OF DRAWINGS

In the Figures, which are not drawn to scale, but are setforth to illustrate various manufactures of the invention, the Figures are as follows.

In the Figures, and in the specification, like parts and like ingredients, are identified by like numbers. The terms that appear earlier in the specification, and in the description of the Figures, as well as in embodiments thereof, are further described in the specification.

DETAILED DESCRIPTION OF DRAWINGS

Figure 1:
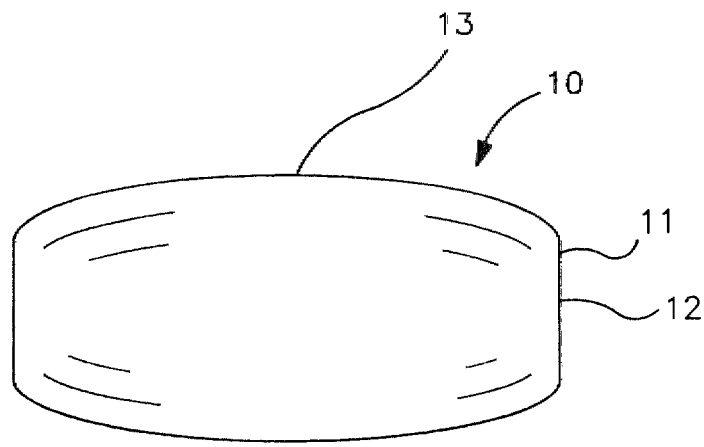
FIG. 1, is a general view of a dosage form provided by this invention, that is designed, shaped and adapted for the oral administration of a drug at a controlled rate over an extended time to a human patient in need of drug therapy.

Turning attention now to the Figures in detail, which Figures are examples of a dosage form and a drug composition provided by this invention, and which examples are not to be construed as limiting the invention, one example of a dosage form is seen in FIG. 1. In FIG. 1, a dosage form 10 is seen comprising a body member 11 that comprises an exterior wall 12. The exterior wall 12 surrounds an interior wall and an internal compartment, not seen in FIG. 1. Dosage form 10 comprises at least one exit 13 that connect the exterior environment, such as the gastrointestinal tract of a human patient, with the interior of the dosage form.

Figure 2:
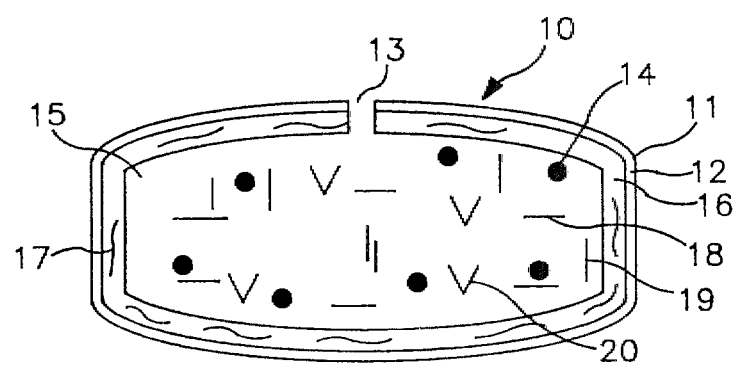
FIG. 2, is a general view of the dosage form of FIG. 1, in opened section, depicting a dosage form provided by this invention comprising an internally housed pharmaceutically-acceptable drug composition surrounded by an interior and exterior wall.

Dosage form 10, of FIG. 2, illustrates a dosage form that possesses controlled-release delivery kinetics. The dosage form delivers a drug, or a drug and its pharmaceutically-acceptable salt to a patient in need of drug therapy. The terms "therapeutic agent" and "drug" as used interchangeably herein. The phrase, controlled-release denotes the dosage form provides a linear drug release with time, a zero order delivery rate or an ascending release profile of drug. Dosage form 10 controls or governs the delivery of drug 14, represented by dots 14, from an internal space or compartment 15. Dosage form 10 delivers drug 14 at a measured rate per unit time over an extended or sustained-release period of about 30 minutes to about 30 hours, more preferably about 6 hours to about 24 hours, and even more preferably about 4 hours to about 24 hours.

The dosage forms provided by this invention, are useful for establishing therapeutic drug levels in the blood, including the plasma, for therapy. Dosage form 10, as seen in the accompanying figures, embraces the shape of a dosage tablet, and it can embrace the shape of a caplet, or a buccal, or a sublingual dosage form. The sustained-release dosage form of this invention provides extended-continuous delivery greater than conventional, noncontrolled tablets, or noncontrolled-nonsustained release tablets and/or capsules that exhibit a dose-dumping of their drug.

Dosage form 10 of FIG. 2, comprises exterior wall 12 that surrounds internal compartment 15. Exterior wall 12 comprises totally, or in at least a part a semi-permeable composition. The semipermeable composition is permeable to the passage of an aqueous or an aqueous-biological fluid present in the gastrointestinal tract, and exterior wall 12 is impermeable to the passage of drug 14. Exterior wall 12 is nontoxic, and it maintains its physical and chemical integrity during the dispensing time of drug 14. The phrase "maintains its physical and chemical integrity" means the exterior wall 12 does not lose its structure, and it does not undergo a chemical change during the dispensing of drug 14.

Exterior wall 12 comprises a composition that does not adversely affect an animal, a human, or components of the dosage form. Compositions for forming exterior wall 12 are, in one embodiment, comprised of a member selected from the group consisting a cellulose ester polymer, a cellulose ether polymer and a cellulose ester-ether polymer. These cellulosic polymers have a degree of substitution, DS, on the anhydroglucose unit, from greater than 0 up to 3 inclusive. By "degree of substitution" is meant the average number of hydroxyl groups originally present on the anhydroglucose unit comprising the cellulose polymer that are replaced by a substituting group. Representative exterior wall 12 polymers comprise a member selected from the group consisting of cellulose acylate, cellulose diacylate, cellulose triacylate, cellulose acetate, cellulose diacetate, cellulose triacetate, mono-, di- and tricellulose alkanylates, mono-, and di- and tricellulose alkinylates. Exemplary polymers include cellulose acetate having a DS of up to 1 and an acetyl content of up to 31 weight %; cellulose acetate having a DS of 1 to 2 and any acetyl content of 21 to 35%; cellulose acetate having a DS of 2 to 3 and an acetyl content of 35 to 44.8%; and the like. More specific cellulosic polymers comprise cellulose propionate having a DS of 1.8, a propyl content of 39.2 to 45% and a hydroxyl content of 2.8 to 5.4%; cellulose acetate butyrate having a DS of 1.8, an acetyl content of 13 to 15% and a butryl content of 17% to 53% and a hydroxyl content of 0.5 to 4.7%; cellulose triacylates having a DS of 2.9 to 3, such as cellulose trivalerate, cellulose trilaurate, cellulose tripalmitate, cellulose trisuccinate and cellulose trioctanoate; celluloses diacylate having a DS of 2.2 to 2.6, such as cellulose disuccinate, cellulose dipalminate, cellulose dioctanoate, cellulose dipentanoate, co-esters of cellulose, such as cellulose acetate butyrate, and cellulose acetate propionate, and blends of the above.

Additional semipermeable polymers comprise acetaldehyde dimethylcellulose acetate; cellulose acetate ethylcarbamate; cellulose acetate methylcarbamate; cellulose diacetate propylcarbamate; cellulose acetate diethylaminoacetate; ethyl acrylate methyl methacrylate, semipermeable polyamide; semipermeable polyurethane; semipermeable sulfonated polystyrene; semipermeable crosslinked selective polymer formed by the coprecipitation of a polyanion and polycation, as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable, lightly crosslinked polystyrenes; semipermeable crosslinked poly (sodium styrene sulfonate); semipermeable cross-linked poly (vinylbenzyltrimethyl ammonium chloride); and semipermeable polymers possessing a fluid permeability in the range of $2.5 \times 10^{-8}$ to $5 \times 10^{-2}$ (cm$^2$/hr·atm), expressed per atmosphere of hydrostatic or osmotic pressure difference across the semipermeable exterior wall 12. The polymers are known to the polymer art in U.S. Pat. Nos. 3,845,770; 3,916,899 and 4,160,020; and in *Handbook of Common Polymers*, by Scott, J. R. and Roff, W. J. 1971, CRC Press, Cleveland, Ohio. Exterior wall 12, in a present manufacture can be coated from a substantially single solvent system, such as acetone if coated from a solution, or water if coated as a dispersion.

Dosage form 10 comprises an interior wall 16. The interior wall 16 faces internal compartment 15, and exterior wall 12. Exterior wall 12 comprises a surface that faces the environment of use. Internal compartment 15 is defined by a bilayer membrane system comprising interior wall 16 and exterior wall 12 wherein interior wall 16 and exterior wall 12 are in contacting relationship. The fluid permeability of interior wall 16 is responsive to the osmolarity or osmolality of fluid contacting the interior wall 16 or the osmotic core within the internal compartment 15. In preferred embodiments, the fluid permeability of interior wall 16 increases in response to a decrease in the osmolarity of the osmotic core. Compositions for forming interior wall 16 comprise a hydrophobic substance and a hydrophilic substance wherein hydrophilicity of the hydrophilic substance is osmosensitive. Preferably, the hydrophilic substance exhibits an aqueous solubility responsive to osmotic pressure and/or ionic strength of the osmotic core. More preferably, the hydrophilic substance provides increased permeability of interior wall 16 in response to a decrease in the osmotic pressure or the ionic strength of the osmotic core. Examples of hydrophilic substances include, but are not limited to, ethylcellulose. Examples of hydrophilic substances include, but are not limited to, hydroxyalkylcellulose comprising an alkyl of 1 to 5 carbons, e.g., hydroxypropylcellulose.

In alternative embodiments, the interior wall comprises a polymer composition, including compositions used for forming exterior wall, as described above. Preferably, the hydrophilic substance exhibits an aqueous solubility responsive to degree of hydration of the polymer composition.

Additional compositions for forming interior wall 16 include, but are not limited to, polypeptides; proteins such as gelatin, collagen, keratin, casein, ammonium casein, calcium casein, magnesium casein, potassium casein, sodium casein, zein, and the like; peptides, such as hydrolyzed vegetable protein, hydrolyzed milk protein, and the like; polysaccharides such as acacia gum, agar, dammar gum, gellum gum, guar gum, locust bean gum, xanthan gum, tragacanth gum, tamarind gum, ghatti gum, konjac gum, carrageenans, laminaran, alginic acid, sodium alginate, calcium alginate, potassium alginate, propylene glycol alginate, ammonium alginate, hyaluronic acid, pectin, amylopectin, arabinoglactan, dextrin, cyclodextrin, maltodextrin, polydextrin, amylase, starch, modified starch, hydroxypropyl starch, starch acetate, starch esters, starch ether-esters, starch ether-hemiacetals, starch phosphate, starch sodium octenyl succinate, starch sodium succinate, sodium starch glycolate, starch graft copolymer, pregelatinized starch, furcellaran, n-vinyl lactam polysaccharides and the like; cellulose derivatives such as sodium carboxymethylcellulose, potassium carboxymethylcellulose, hydroxyethyl cellulose, hydroxypropyl cellulose, methyl cellulose, hydroxypropyl methylcellulose, hydroxypropyl methylcellulose phthalate, hydroxypropyl methylcellulose acetate succinate, low-substituted cellulose acetate, cellulose sulfate, cellulose phosphate, hydroxyethyl methylcellulose, chitosan, derivatized chitin, hydroxyethylchitin and the like; surfactants such as sorbitan fatty acid esters, polyoxyethylene alkyl ethers, polyoxyethylene fatty acid esters, glycerol monostearate, acetylated monoglycerides, polyethoxylated castor oil, polyoxyethylene polyoxypropylene copolymer, cetostearyl alcohol, ethoxylated mono and diglycerides, lecithin, hydroxylated lecithin, polyethylene glycol stearate, and the like; synthetic polymers such as polyacrylic acid, sodium polyacrylic acid, potassium polyacrylic acid, polyvinyl alcohol, polyvinyl acetate phthalate, poly(hydroxyalkyl methacrylate), polyethylene glycol, polyoxyethylene, polyvinyl pyrrolidone, vinyl pyrrolidone vinyl acetate copolymer, sodium poly(vinylsulfonic acid), ammonium poly(vinylsulfonic acid), poly(stryrenesulfonic acid, sodium poly(systrenesulfonic acid), potassium poly(styrene sulfonic acid), poly(vinylphosphonic acid) salts, poly(maleic acid), poly(4-vinylbenzoic acid) salts, poly(3-vinyloxypropane-1-sulfonic acid) salts, poly(4-vinylphenol) salts, poly(n-vinyl-succinamidic acid) salts, polyacrylamides, polyamines, polyimines, and the like; inorganic polymers such as aluminium hydroxide, bentonite, hectorite, laponite, poly(silicic acid), sodium poly(silicic acid), potassium poly(silicic acid), and the like; eucheurn, fucoidan, hypnea and glycyrrhizin.

Additional compositions for forming interior wall 16 include hydrogel polymers, expandable osmopolymers, osmotically effective compounds, suspending agents, compounds for forming passageway and pore formers as defined in greater detail below.

In a preferred embodiment, as illustrated in FIG. 2, interior wall 16 comprises ethylcellulose, one hundred weight percent, (100 wt %), or in another manufacture a composition comprising a blend of 40 to 99 wt % ethylcellulose and 1 to 60 wt % hydroxyalkylcellulose with the total weight of the compositional blend equal to 100% wt. The ethylcellulose used for the interior wall is nontoxic, insoluble in water, and insoluble in gastrointestinal fluid. The interior ethylcellulose wall is coated from a single anhydrous solution, or the interior ethylcellulose wall is coated from a dispersion comprising the single solvent water. The ethylcellulose used for the purpose of this invention comprises a 15 to 60 wt % ethoxy content, a viscosity of 4 to 200 centiposes, or higher, and a 5,000 to 1,250,000 weight average molecular weight. The hydroxypropylcellulose is homogeneously blended with the ethylcellulose, and is identified by a wavy line 17 in interior wall 16. The hydroxypropylcellulose 17 in interior wall 16 comprises a 7,500 to 1,500,000 weight-average molecular weight, and it is soluble in water below 40° C. and in ethyl alcohol and displays a solubility in water which sensitive to osmotic pressure or ionic strength.

Interior wall 16 comprising hydroxypropylcellulose provides unexpected properties for this invention. For instance, ethylcellulose is hydrophobic and accordingly its fluid permeability is low which hinder sufficient water flux passing through interior wall 16 to provide a wide-range of delivery rates. This invention, enhances the fluid permeability of interior wall 16 by blending a hydrophilic substance, such as a fluid flux enhancer, wherein hydrophilicity of the hydrophilic substance is osmosensitive. Preferably, the hydrophilic substance exhibits an aqueous solubility responsive to osmotic pressure and/or ionic strength of the osmotic core. More preferably, the hydrophilic substance increases the permeability of the interior wall 16, e.g., ethylcellulose wall, in response to a decrease in the osmotic pressure or the ionic strength of the osmotic core. In certain embodiments, as the hydrophilic substance is dissolved and/or leached from the interior wall 16, it provides fluid-control pores, resulting in increased permeability of interior wall 16. In alternative embodiments, the hydrophilic substance exhibits an aqueous solubility responsive to degree of hydration of the polymer composition.

If the dosage form is manufactured with a single wall comprising a composition of ethylcellulose and hydroxypropylcellulose, as the pores are formed, the pores allow lipids which are present in the gastrointestinal tract to sorb into this unprotected wall, which leads to an unacceptable change in this nonprotected single wall. That is, the hydrophobic lipids cause the unprotected wall to become soft, flaccid and tearable as the lipid functions as a plasticizer within the ethylcellulose. The presence of the sorbed lipids cause the porous wall to become hydrophobic again, thereby reversing the desirable effects of the hydrophilic flux enhancer. The present invention unexpectedly discovered by providing an outside wall comprising a cellulose acylate, the outside wall excludes and prevents the lipids of the gastrointestinal tract from contacting and reaching the interior wall. The membrane system provides a wide range of low to high fluxes. In a preferred embodiment, the membrane system comprises an interior wall composed of ethylcellulose and hydroxypropylcellulose and an exterior wall comprised of cellulose acylate. In an alternative embodiment, the membrane system comprises an interior wall composed of cellulose acylate and hydroxypropylcellulose and an exterior wall comprised of cellulose acylate. An additional advantage provided by the present invention is each wall can be coated from a single solvent to provide reproducible interior and exterior walls with reproducible permeability and mechanical properties.

In FIG. 2, internal compartment 15 comprises a single homogenous composition. The compartment 15 comprises therapeutic agent 14, represented by dots. The term therapeutic agent as used herein included medicines or drugs, nutrients, vitamins, food supplements, and other beneficial agents that provide a therapeutic or a benefit to animals, including a warm-blooded animal, humans, farm animals, and zoo animals. Representative of drugs 14 comprises an opioid analgesic selected from the group consisting of alfentanil, allylprodine, alphaprodine, anileridine, benzylmorphine bezitramide, buprenorphine, butorphanol, clonitazene, codeine, cyclazocine, desomorphine, dextromoramide, dezocine, diampromide, dihydrocodeine, dihydromorphine, dimenoxadol, diepheptanol, dimethylthiambutene, dioxaphetyl butyrate, dipipanone, eptazone, ethoheptazine, ethylmethylthiambutene, ethylmorphine, propylmorphine, etonitazene, fentanyl, heroin, hydrocodone, hydromorphone, hydroenitabas, hydrocypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphone, phenazocine, phenoperidine, piminodine, pirtramide, propheptazine, promedol, properidine, propiram, propoxyphene, sufentanil, tramadol, and tilidine. The dose of opioid drug 14 is 0.1 μg to 700 mg. Additional examples of therapeutic agents for use in the instant invention are described in U.S. Pat. No. 5,082,668, which is incorporated herein by reference.

The opioid analgesic 14 can be present in compartment 15 alone, or the opioid analgesic 14 can be present with a nonopioid analgesic 14. Examples of nonopioid analgesic comprise a member selected from the group consisting of acetaminophen, aminobenzoate potassium, aminobenzoate sodium, aspirin, benoxaprofen, benzydamine, bicifadine decibuprofen, fenoprofen, flurbiprofen, ibufenac, indoprofen, ibuprofen, ketoprofen, naproxen, naproxol, salicylamide, sodium salicylate, and salicylate potassium. The dose of nonopioid analgesic 14 is 0.5 mg to 600 mg. An analgesic composition in compartment 15 comprises 1.0 mg to 750 mg of both the opioid analgesic and nonopioid analgesic.

The analgesic drug comprising the opioid analgesic and the nonopioid analgesic can be present as the free base, free acid, or as a therapeutically acceptable derivative, or as a therapeutically acceptable salt. The therapeutically acceptable salts comprise inorganic salts, organic salts, including hydrobromide, hydrochloride, mucate, N-oxide, sulfate, acetate, phosphate dibasic, phosphate monobasic, acetate trihydrate, bi(heptafluorobutyrate), bi(methylcarbamate), bi(pentafluoropropionate), bi(pyridine-3-carboxylate), bi(trifluoroacetate), bitartrate, chlorhydrate, and sulfate pentahydrate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, and procaine, aluminum, calcium, lithium, magnesium, potassium, sodium propionate, zinc, and the like.

Dosage form 10, in compartment 15 comprises a pharmaceutically acceptable polymer hydrogel 18, as represented by horizontal dashes. Representative polymer hydrogels comprise a maltodextrin polymer comprising the formula $(C_6H_{12}O_5)\lambda.H_2O$, wherein $\lambda$ is 3 to 7,500, and the maltodextrin polymer comprises a 500 to 1,250,000 number-average molecular weight; a poly(alkylene oxide) represented by poly (ethylene oxide) and poly(propylene oxide) having a 50,000 to 750,000 weight-average molecular weight, and more specifically represented by a poly(ethylene oxide) of at least one of 100,000, 200,000, 300,000, or 400,000 weight-average molecular weights; an alkali carboxyalkylcellulose, wherein the alkali is sodium, lithium, potassium or calcium, and alkyl is 1 to 5 carbons such as methyl, ethyl, propyl or butyl of 10,000 to 175,000 weight-average molecular weight; and a copolymer of ethylene-acrylic acid, including methacrylic and ethacrylic acid of 10,000 to 1,500,000 number-average molecular weight. The therapeutic composition comprises 5 to 400 mg of a polymer hydrogel. The therapeutic composition can be manufactured into dosage form 10 and it can be used as the therapeutic composition for its therapeutic effect. The hydrogel polymer exhibits an osmotic pressure gradient across bilayer interior wall and exterior wall thereby imbibing fluid into compartment 15 to form a solution or a suspension comprising drug 14 that is hydrodynamically and osmotically delivered through a passageway from dosage form 10.

Dosage form 10 comprises a binder 19 represented by vertical dashes 19. The binder imparts cohesive qualities to the composition. Representative materials useful for this invention as binders comprise a member selected from the group consisting of starch, gelatin, molasses, a vinyl polymer comprises 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinylcaprolactone, poly-n-vinyl-5-methyl-2-pyrrolidone, and poly-n-vinylpyrrolidone copolymers with a member selected from the group consisting of vinyl acetate, vinyl alcohol, vinyl chloride, vinyl fluoride, vinyl butyrate, vinyl laureate, and vinyl stearate, methylcellulose, hydroxypropylcellulose, hydroxypropylmethylcellulose, and mixtures of binders. The binders can be used as a solution, or in a dry form to prepare the therapeutic composition. The therapeutic composition comprises 0 to 100 mg of a binder and in a present manufacture from 0.01 to 50 mg of the binder.

Dosage form 10 comprises a lubricant 20 represented by the letter v. The lubricant is used during manufacture of the composition to prevent sticking to die walls or punch faces, generally to lessen adhesion. The lubricants are selected from the group consisting of polyethylene glycol, sodium stearate, oleic acid, potassium oleate, caprylic acid, sodium stearyl fumarate, magnesium palmitate, calcium stearate, zinc stearate, magnesium stearate, magnesium oleate, calcium palmitate, sodium suberate, potassium laureate, stearic acid, salts of fatty acids, salts of alicyclic acids, salts of aromatic acids, oleic acid, palmitic acid, a mixture of a salt of a fatty, alicyclic or aromatic acid, and a mixture of magnesium stearate and stearic acid. The amount of lubricant in the therapeutic composition is 0.01 to 20 mg.

Figure 3:
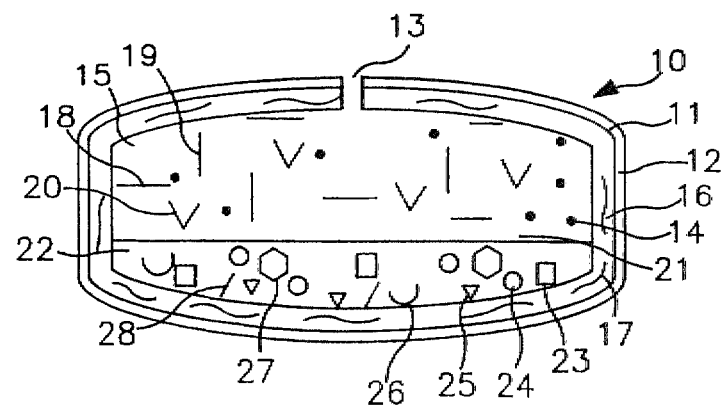
FIG. 3, is an opened view of FIG. 1, illustrating a dosage form comprising a drug composition, and a separate but initially contacting push-displacement composition comprising means for pushing the drug composition from the dosage form with both compositions surrounded by an interior wall and an exterior wall.

FIG. 3 depicts dosage form 10 in opened section illustrating internal compartment 15. Internal compartment comprises the therapeutic composition containing drug 14, as described in detail in FIG. 2. The therapeutic composition of FIG. 2 is identified further in FIG. 3 as drug layer 21. Drug layer 21 comprises the ingredients described in FIG. 2 and the details previously disclosed are included in this description of FIG. 3. Drug layer 21 in FIG. 3 initially is in contact with push layer 22.

In FIG. 3, an expandable layer, alternatively referred to as a push layer 22 comprises 10 mg to 400 mg of an expandable osmopolymer 23 represented by squares. The osmopolymer 23 in layer 22 possesses a higher molecular weight than the hydrogel polymer 18 in the drug composition. The osmopolymer 23 comprises a member selected from the group consisting of a polyalkylene oxide and, a carboxyalkylcellulose and acrylates. The polyalkylene oxide possesses a 1,000,000 to 10,000,000 weight-average molecular weight. Representative of polyalkylene oxide include a member selected from the group consisting of polymethylene oxide, polyethylene oxide, polypropylene oxide, polyethylene oxide having a 1,000,000 molecular weight, polyethylene oxide possessing a 2,000,000 molecular weight, polyethylene oxide comprising a 3,000,000 to 8,000,000 molecular weight, polyethylene oxide comprising a 7,000,000, and 7,800,000 molecular weight, and cross-linked polymethylene oxide possessing a 1,000,000 molecular weight, and polypropylene oxide of 1,200,000 molecular weight. Typical osmopolymer 23 carboxyalkylcellulose in the expandable layer 22 comprises a 200,000 to 7,250,000 weight-average molecular weight. Representative carboxyalkylcellulose comprises a member selected from the group consisting of alkali carboxyalkylcellulose, sodium carboxymethylcellulose, lithium carboxyethylcellulose, calcium carboxymethylcellulose, potassium carboxymethylcellulose, sodium carboxyethylcellulose, lithium carboxyalkylhydroxy-alkylcellulose, sodium carboxyethylcellulose, carboxyalkylhydroxyalkylcellulose, carboxymethylhydroxyethylcellulose, carboxethylhydroxyethylcellulose and carboxymethylhydroxypropylcellulose. Typical osmopolymer 23 acrylates comprise non-crosslinked polyacrylic acid, and polyacrylic acids crosslinked with allyl sucrose, allylpentacrythritol, or divinyl glycol, sodium or potassium polyacrylic acid, and the like. The osmopolymers used for the push-expandable layer exhibit an osmotic pressure gradient across semipermeable exterior wall 12. The osmopolymers imbibe fluid into dosage form 10, thereby swelling, expanding as a hydrogel or osmogel, whereby, they push the drug from the osmotic dosage form.

Push layer 22 comprises 0 to 200 mg, and presently 0.5 to 75 mg of an osmotically effective compound 24, represented by circles. The osmotically effective compounds are known also as osmagents and as osmotically effective solutes. They imbibe an environmental fluid, for example, from the gastrointestinal tract, into dosage form 10 for contributing to the delivery kinetics of push layer 22 and to the permeability characteristics of the interior wall 16. Representative of osmotically active compounds comprise a member selected from the group consisting of osmotic salts, such as sodium chloride, potassium chloride, magnesium sulfate, lithium phosphate, lithium chloride, sodium phosphate, potassium sulfate, sodium sulfate, potassium phosphate, osmotic carbohydrates; glucose, fructose, maltose and sorbitol; urea; osmotic acids; tartaric acid; citric acid; potassium acid phosphate; and a mixture of sodium chloride and urea.

Push layer 22 comprises 0 to 75 mg of a suspending agent used for providing stability and homogenicity to push layer 22. Suspending agent 25, represented by clear triangles comprises a hydroxypropylalkylcellulose that comprises an alkyl of 1 to 7 carbons, straight or branched, with the hydroxypropylalkylcellulose possessing a 9,000 to 450,000 number-average molecular weight. The hydroxypropylalkyl-cellulose is represented by a member selected from the group consisting of hydroxypropylmethylcellulose, hydroxypropylethylcellulose, hydroxypropylisopropyl-cellulose, hydroxypropylbutylcellulose and hydroxypropylpentylcellulose. Push layer 22 optionally comprises a hydroxyalkylcellulose, also represented by triangles 25. The hydroxyalkylcellulose is a viscosity-increasing suspending agent comprises a member selected from the group consisting of hydroxymethylcellulose, hydroxyethylcellulose, hydroxypropylcellulose and hydroxybutylcellulose comprising a 7,500 to 1,000,000 viscosity-average molecular weight. The suspending agent include also polyvinylpyrrolidone, acacia, agar, locust bean gum, alginic acid, gum karaya, gum tragacaroth, carrageenan, gum ghatti, guar gum, xanthan gum, and bentonite.

Push layer 22 comprises 0 to 5 mg of a nontoxic colorant, or dye 26 identified by a half-circle. The colorant 26 makes the dosage form more esthetic in appearance, and it serves to identify the dosage form during manufacture and during therapy. The colorants include Food and Drug Administrations Colorant (FD&C), such as FD&C No. 1 blue dye, FD&C No. 4 red dye, FD&C yellow No. 5, FD&C yellow No. 6, FD&C blue No. 2, FD&C green No. 3, FD&C cranberry red No. 40, red ferric oxide, yellow ferric oxide, black ferric oxide, titanium dioxide, carbon black, Opadry® comprising polycellulose, or starch, or cured polymers with dyes commercially available from Colorcon Corporation, West Point, Pa.; erythrosine, allura red, sunset yellow and chlorophylls.

A lubricant 27, identified by hexagon is formulated into push-expandable layer 22. Typical lubricants comprise a member selected from the group consisting of polyethylene glycol, sodium stearate, potassium stearate, magnesium stearate, stearic acid, calcium stearate, sodium oleate, calcium palmitate, sodium laurate, sodium ricinoleate, potassium linoleate, glyceryl monstearate, glyceryl palmitostearate, halogenated castor oil, sodium lauryl sulfate, sodium stearyl fumarate, and zinc stearate. The amount of antiadherent lubricant in layer 22 is 0.01 to 10 mg.

An antioxidant 28, represented by right slanted dashes, is present in push-expandable formulation 22 to inhibit the oxidation of ingredients comprising expandable formulation 22. Expandable formulation 22 comprises 0.00 to 5 mg of an antioxidant. Representative antioxidants comprise a member selected from the group consisting of absorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium ascorbate, sodium bisulfate, sodium metabisulfate, sorbic acid, potassium ascorbate, vitamin E, 4-chloro-2-,6-ditertiary butylphenol, alphatocopherol, and propylgallate. The antioxidant slow, or prevent the oxidization of the dosage form and its ingredients by atmospheric oxygen.

Dosage form 10, comprises another manufacture provided by the invention. Dosage form 10 comprises an overcoat not shown on the outer surface of exterior wall 12 of dosage form 10. The overcoat is a therapeutic composition comprising 0.5 to 200 mg of drug and 0.5 to 275 mg of a pharmaceutically acceptable carrier selected from the group consisting of alkylcellulose, hydroxyalkylcellulose and hydroxypropylalkylcellulose. The overcoat is represented by methylcellulose, hydroxyethylcellulose, hydroxybutylcellulose, hydroxypropylcellulose, hydroxypropylmethylcellulose, hydroxypropylethylcellulose and hydroxypropylbutylcellulose. The overcoat, carried by the outer surface of the exterior wall 12 distant from the compartment 15 and it can be formulated with 0 to 50 wt % of a plasticizer, opacificer, colorant, or antitack agent, not seen in FIG. 4. The overcoat provides therapy immediately as the overcoat dissolves or undergoes dissolution in the presence of gastrointestinal fluid and concurrently therewith delivers the drug into the gastrointestinal tract for immediate drug therapy.

Dosage form 10, manufactured as an osmotically controlled-release dosage form, comprises at least one passageway 13. The phrase "controlled-release" as used herein indicates that control is exercised over both the duration and the profile of the drug release pattern. Preferably, the therapeutic agent is delivered in an extended-linear, non-declining release profile over a period of about 30 minutes to about 30 hours, more preferably about 6 hours to about 24 hours, and even more preferably about 4 hours to about 24 hours. In preferred embodiments, the extended-linear release profile is a zero order release profile. In an alternative embodiment, the extended-linear release profile is an ascending release profile. An ascending release profile is preferred when delivering drugs that are not well absorbed in the lower gastrointestinal tract as compared to the upper tract. Thus the higher drug delivery rate at later hours compensates for the lower absorption to result in more even plasma concentrations.

The expression "passageway" as used for the purpose of this invention, includes aperture, orifice, bore, pore, porous element through which drug 14 can be pumped, diffuse or migrate through a fiber, capillary tube, porous overlay, porous insert, microporous member, and porous composition. The passageway 13 includes also a compound that erodes or is leached from exterior wall 12 in the fluid environment of use to produce at least one passageway. Representative compounds for forming a passageway include erodible poly(glycolic) acid, or poly(lactic) acid in the wall; a gelatinous filament; a water-removable poly(vinyl alcohol); leachable compounds such as fluid-removable pore-forming polysaccharides, acids, salts, or oxides. A passageway can be formed by leaching a compound from exterior wall 12, such as sorbitol, sucrose, lactose, maltose or fructose, to form a controlled-release dimensional pore-passageway. The passageway can have any shape, such as round, triangular, square and elliptical, for assisting in the controlled-metered release of drug 14 from the dosage form. The dosage form can be manufactured with one or more passageways for example two passageways, in spaced-apart relation on one or more surfaces of the dosage form. A passageway and equipment for forming a passageway are disclosed in U.S. Pat. Nos. 3,845,770 and 3,916,899 by Theeuwes and Higuchi; in U.S. Pat. No. 4,063,064 by Saunders et al.; and in U.S. Pat. No. 4,088,864 by Theeuwes et al. Passageways comprising controlled-release dimensions sized, shaped and adapted as a releasing-pore formed by aqueous leaching to provide a releasing-pore of a controlled-release rate are disclosed in U.S. Pat. Nos. 4,200,098 and 4,285,987 by Ayer and Theeuwes.

Figure 4:
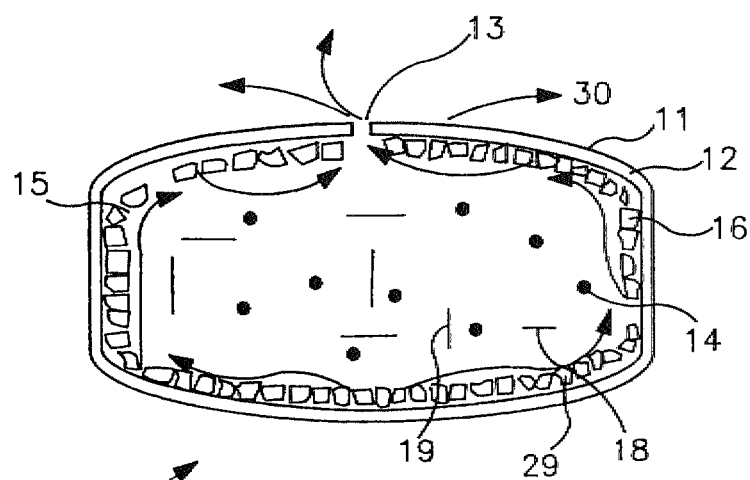
FIG. 4, is an opened view of the dosage form of FIG. 1, depicting the dosage form in operation as a fluid sensitive pore former begins to dissolve, and is eluted from the interior wall to increase the porosity of the interior wall, while simultaneously keeping the physical and chemical integrity of the exterior wall.

FIG. 4 illustrates dosage form 10 in operation during a drug 14 delivery period. The illustrated dosage form 10 comprises an exterior wall 12 and an interior wall 16. The exterior wall 12 maintains its physical and chemical integrity throughout the drug delivery period. Interior wall 16 comprises a hydrophilic substance 29, for example, a pore former, that is aqueous soluble at an osmotic pressure of 8 atmospheres, which 8 atmospheres generally is the osmotic pressure of the gastrointestinal tract of a human. The hydrophilic substance 29, in one manufacture, is a pharmaceutically acceptable polymer that exhibits an aqueous solubility which is sensitive to osmotic pressure, which polymer is soluble at low osmotic pressure and insoluble or slowly soluble at higher osmotic pressure. Representative of other acceptable hydrophilic substances, also referred to as pore formers, include alkali metal salts such as lithium carbonate, sodium chloride, potassium chloride, and potassium sulfate; alkaline earth metal salts such as calcium phosphate, and calcium nitrate; transition metal salts such as ferric chloride, ferrous sulfate, and zinc sulfate; polysaccharides including mannitol, mannose, galactose, aldohexose, altrose, talose and sorbitol. The osmotic pressure can be measured by Model 302B, Vapor Pressure Osmometer, manufactured by the Hewlett Packard, Co., Avondale, Pa. A hydrophilic substance, e.g., a pore forming polymer, is represented by hydroxypropylcellulose possessing a weight-average molecular weight of 80,000 grams per mole. Dosage form 10, when initially placed into an aqueous environment, or into a fluid biological environment, exhibits a slow drug delivery until pore former 29 dissolves or is leached from interior wall 16. For example, after a period of time, often 1 to 2 hrs, the osmotically-sensitive hydrophilic substance 29 begins to dissolve and is eluted from interior wall 16. This operation, provides a continuous and seamless interior wall 16 with hydrophilic substance 29 being hydrodynamically and osmotically pumped as seen by multi-arrows 30 from dosage form 10. The eluted hydrophilic substance 29 causes the permeability of interior wall 16 to increase, which correspondingly causes the net permeability of bilaminated interior wall 16-exterior wall 12 to increase over time. This unexpected result provided by this invention, with its increase in permeability offsets any decrease in osmotic activity and produces a linear drug delivery profile. In preferred embodiments, the drug delivery profile is a zero order release profile. In an alternative embodiment, the drug delivery profile is an ascending release profile.

The permeability of a wall can be measured according to a procedure which involves measuring the flow of water through the membrane as a result of osmotic driving force. The measurement is first conducted with a single layer membrane which represents the exterior wall, then the measurements are conducted with bilayer membranes with the exterior and interior walls in parallel arrangement. First, an exterior wall membrane is clamped in a vertical orientation between the two chambers which are commonly referred to as Franz cells. One chamber is filled with distilled water which has an osmotic pressure of zero while the adjoining chamber is filled with a solution of known osmotic pressure, such as a saturated solution of potassium chloride which has an osmotic pressure of 245 atmospheres or of saturated lactose solution which has an osmotic pressure of 20 atmospheres. The osmotic pressure of such osmotic reference solutions are measured using standard freezing point depression measurements or vapor pressure osmometry. Vapor pressure osmometers are available, for example, from Knauer & Co GMBH, Berlin, West Germany. The membrane is thus exposed on one side to pure water and exposed to the osmotic reference solution on the opposite side. Prior to making measurements, a graduated pipette is attached to the chamber holding the osmotic reference solution. Both chambers also contain magnetic stirrers and both chambers are also immersed in a thermal jacket. While measurements are taken, both cells are stirred by way of an external magnetic stirrer and both are maintained at a fixed temperature. The fixed temperature is maintained by continuously passing a thermostated fluid, such as water at 37° centigrade, through the thermal jacket.

The Franz cells and stirring equipment are available from Crown Glass Company, Somerville, N.J.

Water is imbibed by osmosis from the pure water side through the membrane to the solution side. The rate of water flowing through the membrane is measured by monitoring the volumetric flow as a function of time as reflected in the rise in column of solution within the graduated pipette. The thickness and exposed surface area of the membrane are also measured. These dimensional measurements are performed with standard measuring instruments such as with calipers or a tool maker's microscope. Then, given the volumetric flow rates and these measurements, the osmotic permeability of the external wall, $K_e$, is calculated according to the following Equation as:

$$K_e = \frac{(dV/dt) \cdot h_e}{\Pi A} \quad (1)$$

where (dV/dt) is volumetric flow rate, $h_e$ is membrane thickness of the exterior wall, $\Pi$ is osmotic pressure, and A is membrane area.

After the permeability of the exterior wall is determined, the membrane system is then mounted in the Franz cell. The membrane system is oriented such that the interior wall faces the osmotic reference solution and the exterior wall faces the pure water reference. The osmotic water flux is then measured across the bilayer membrane according to the above procedures. The osmotic water flux is inversely proportion to the series resistance provided by the exterior wall and the interior wall and directly proportional to the osmotic pressure, as described by Equation 2:

$$dV/dt = \frac{\Pi}{(h_e/K_e A) + (h_i/K_i A)} \quad (2)$$

where $h_e$ is thickness of exterior wall, $K_e$ is permeability of exterior wall, $h_i$ is thickness of interior wall, and $K_i$ is permeability of interior wall. Rearranging Equation 2 yields the permeability of the interior wall, Equation 3:

$$K_i = \frac{h_i(dV/dt)}{[\Pi A + (h_e/K_e)(dV/dt)]} \quad (3)$$

Given the measured values of volumetric flow rate, thicknesses of the interior wall and exterior wall, the known value for the permeability of the exterior wall, and measured osmotic pressure, the permeability of the interior wall is then calculated from Equation 3. Osmotic reference values of various values ranging from 0 as represented by distilled water to 445 atmospheres as represented by saturated aqueous urea solution can be tested in this format to characterize the effect of osmotic pressure on the permeability of the membrane system. In addition to osmotic pressure, the effect of ionic strength on the permeability of the bilayer system can be measured. The measurements, in this instance, performed with reference solutions of known ionic strength against the distilled water reference as above. The ionic strength of the solution, $\mu$, can be calculated according to standard equations of physical chemistry such as Equation 4:

$$\mu = 0.5[C_1 Z_1^2 + C_2 Z_2^2 + C_3 Z_3^2 + \ldots] \quad (4)$$

where $C_x$ represents the molar concentration of any ion x in the solution and $Z_x$ represents the corresponding valence of ion x. Reference solutions of a simple salt such as sodium chloride can be prepared as the ionic strength reference. Since the value of each ionic charge Z is unity for sodium chloride, a value of one for the sodium ion and a value of one for the chloride ion, the ionic strength according to Equation 4 is directly proportional to molar concentration. A saturated solution of sodium chloride consists of 5.5 moles per liter and therefore has an ionic strength of 5.5 moles per liter. Such a saturated solution can be serially diluted with distilled water to produce a series of ionic strength reference solutions of any value less than 5.5 moles per liter for use in the reference cell to determine the effect of ionic strength on the permeability of a membrane system as a function of ionic strength.

Hydrophilic materials for use in forming the interior wall which have solubilities sensitive to osmotic pressure or to ionic strength can be screened experimentally prior to formulating them within the interior wall. This procedure involves forming an aqueous solution of the candidate hydrophilic materials using distilled water as the solvent. Then, the resulting solution is cast onto a smooth inert surface, such as a glass plate, and allowed to dry to a film. The film is then removed and cut into sections of known area, thickness, and weight. The resulting film samples are then placed in a series of reference solutions of various osmotic pressures or ionic strengths with mild stirring. The time required for the film to dissolve, t, is then measured as a function of osmotic pressure or ionic strength. Then, given the known values of initial film thickness, $h_i$, the dissolution rate of the film, dh/dt, can be calculated according to Equation 5. The factor 2 is introduced to account for simultaneous dissolution from both sides of the film.

$$dh/dt = h_i/2t \quad (5)$$

This screening can also be expanded to include the effect of molecular weight of the hydrophilic material on dissolution rate as a function of osmotic pressure or ionic strength. This can be accomplished by determining the dissolution rate of low molecular weight and high molecular weight pore formers which effect generally follows the trend of faster dissolution rate at lower molecular weight and faster dissolution rate at lower osmotic pressure.

Figure 5:
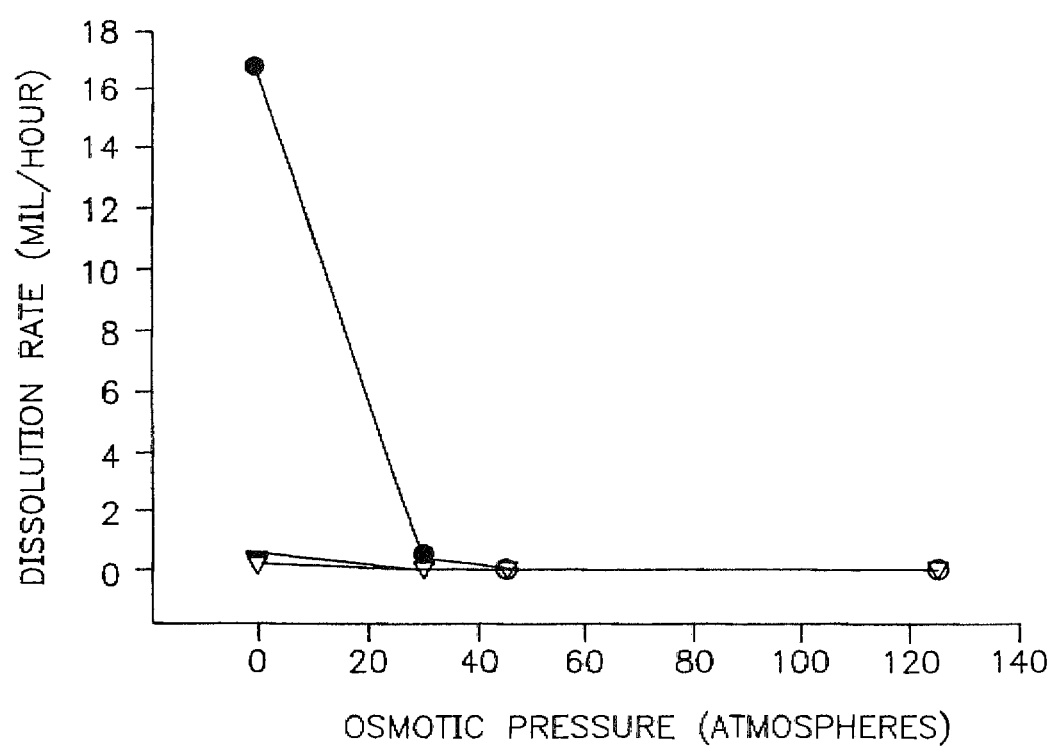
FIG. 5, represents a plot of the dissolution of pore former candidates of the interior wall as a function of osmotic pressure.

FIG. 5 demonstrates the dissolution behavior in the presence of osmotic pressure. The x-axis refers to the osmotic pressure of the test media and the y-axis represents the dissolution rate of hydrophilic materials under the influence of osmotic pressure. The different symbols represent different molecular weight hydrophilic materials initially present within an internal wall. The dark circle represents 80,000 g/mole, the clear circle 190,000 g/mole, the dark triangle 300,000 g/mole, and the clear triangle 1,000,000 g/mole.

In one embodiment, the invention provides a membrane comprising a semipermeable membrane having a control membrane disposed thereon, wherein the water permeability of the control membrane is responsive to changes in the osmolarity of fluid contacting the control membrane. Preferably, the water permeability of the control membrane is inversely proportional to changes in the osmolarity of fluid contacting the control membrane. The composition of the control member corresponds to the composition of the interior wall as described above. The composition of the semipermeable membrane corresponds to the composition of the exterior wall as described in the membrane system above.

In an alternative embodiment, the invention pertains to an osmotic pump comprising an osmotic core; a semipermeable membrane enclosing at least a portion of the core; and a control membrane disposed between at least a portion of the semipermeable membrane and the core, the water permeability of the control membrane being responsive to changes in the osmolarity of the core. Preferably, the water permeability of the control membrane is inversely proportional to changes in the osmolarity of the core. The composition of the control member corresponds to the composition of the interior wall as described above. The composition of the semipermeable membrane corresponds to the composition of the exterior wall as described in the membrane system above.

DESCRIPTION FOR MANUFACTURING THE COMPOSITION AND DOSAGE FORM OF THE INVENTION

The interior wall 16 and the exterior wall 12 of the dosage form can be formed by using an air suspension procedure. This procedure consists in suspending and tumbling a wall-forming composition in a current of air and wall-forming composition until a wall is applied to the drug-forming compositions. The interior wall is formed first followed by the exterior wall. The air suspension procedure is well-suited for independently forming an individual wall. The walls can be formed with a wall-forming composition in a Wurster® air suspension coater. The interior wall can be formed using the solvent ethanol. The exterior wall is formed using an organic solvent, such as acetone-water cosolvent 90:10 to 100:0 (wt:wt) and with 2.5 wt % to 7 wt % polymer solvents. An Aeromatic® air suspension coater can be used for applying both the walls, the interior wall and the exterior wall in successive applications.

Other forming technologies, such as pan coating, can be used for providing the dosage form. In the pan coating system, wall-forming compositions are deposited by successive spraying of the composition or the membrane system, accompanied by tumbling in a rotating pan. A larger volume of cosolvent can be used to reduce the concentration of polymer solids to produce a thinner wall. Finally, the walls of the coated compartments are laser or mechanically drilled, and then dried in a forced air or humidity oven for 1 to 3 days or longer to free the solvent from the dosage form. Generally, the walls formed by these technologies have a thickness of 2 to 20 mils (0.051 to 0.510 mm) with a presently preferred thickness of 2 to 10 mils (0.051 to 0.254 mm).

The dosage form of the invention in another embodiment is manufactured by standard manufacturing techniques. For example, in one manufacture the beneficial drug and other ingredients comprising a therapeutic composition or comprising the drug layer facing the exit means are blended, or the ingredients are blended then pressed, into a solid layer. The drug and other ingredients can be blended with a solvent and formed into a solid or semisolid formed by conventional methods such as ball-milling, calendaring, stirring or roll-milling and then pressed into a selected shape. The drug layer posses dimensions that correspond to the internal dimensions of the area the drug layer is to occupy in the dosage form. Next, the drug layer is placed in contact with the push-displacement layer prepared in a like manner. The layering of the drug layer and the push-displacement layer can be fabricated by conventional press-layering techniques. The membrane system possesses dimensions corresponding to the dimensions of the internal compartment of the dosage form. Finally, the two-layer compartment forming members are surrounded and coated with an inner and outer walls. A passageway is laser drilled or mechanically drilled through the walls to contact the drug layer, with the dosage form optically oriented automatically by the laser equipment for forming the passageway on the preselected drug surface.

In another manufacture, the dosage form is manufactured by the wet granulation technique. In the wet granulation technique the drug and the ingredients comprising the drug layer are blended using a solvent, such as isopropyl alcohol as the granulation fluid. Other granulating fluid, such as water, or denatured alcohol 100% can be used for this purpose. The ingredients forming the drug layer are individually passed through a 40 mesh screen and then thoroughly blended in a mixer. Next, other ingredients comprising the layer are dissolved in a portion of the granulation fluid, such as the solvent described above. Then, the latter prepared wet blend is slowly added to the drug blend with continual mixing in the blender. The granulating fluid is added until a wet blend mass is produced, which wet mass is then forced through a 20 mesh screen onto oven trays. The blend is dried for 18 to 24 hours at 25° C. to 40° C. The dry granules are then screened with a 16 mesh screen. Next, a lubricant is passed through a 60 mesh screen and added to the dry screened granule blend. This procedure is followed for the push-displacement composition. The granulation in both instances, are put into mixing containers and tumble mixed for 2 to 10 minutes. The drug and the push composition are layered and pressed into a layered tablet, for example in a Manesty® layer press.

Another manufacturing process that can be used for providing the drug and push-displacement compositions comprise blending their powdered ingredients in a fluid bed granulator. After the powdered ingredients are dry blended in the granulator, a granulating fluid, for example, poly(vinylpyrrolidone) in a solvent, such as in water, is sprayed onto the respective powders. The coated powders are then dried in a granulator. This process coats the ingredients present therein while spraying the granulating fluid. After the granules are dried, a lubricant, such as stearic acid or magnesium stearate, is blended as above into the mixture. The granules are then pressed in the manner described above. In another embodiment, when the fluid in granulating process is used to manufacture the push-displacement layer, an antioxidant present in the polyalkylene oxide can be removed during the processing step. If antioxidant is desired, it can be added to the push-displacement layer, and this can be accomplished during the fluid bed granulation described above.

The dosage form of this invention is manufactured in another embodiment by mixing a drug with composition-forming ingredients and pressing the composition into a solid layer possessing dimensions that correspond to the internal dimensions of the compartment space adjacent to a passageway. In another embodiment, the drug and other drug composition forming ingredients and a solvent are mixed into a solid, or semi-solid, by conventional methods such as ball-milling, calendaring, stirring, or roll-milling, and then pressed into a preselected, layer-forming shape.

In the general manufactures as presented herein, the manufacture comprising a drug and compositional forming ingredients are placed in contact with the push-displacement layer, and the drug layer and the push layers are surrounded then with the bilayered walls. The layering of the drug composition and the push-displacement composition can be accomplished by using a conventional two-layer tablet press technique. The walls can be applied by molding, spraying or dipping the pressed shapes into wall-forming materials. Another technique that can be used for applying the walls is the air-suspension wall-forming procedure. This procedure consists in suspending and tumbling the two layered drug-push core in a current of air until the wall-forming composition are applied separately to the compartment drug-push layers. Manufacturing procedures are described in *Modern Plastics Encyclopedia*, Vol. 46, pp. 62-70 (1969); and in Pharmaceutical Sciences, by Remington, 14th ed., pp. 1626-1648 (1970) published by Mack Publishing Co., Easton, Pa. The dosage form can be manufactured by following the teaching the U.S. Pat. Nos. 4,327,725; 4,612,008; 4,783,337; 4,863,456; and 4,902,514.

DETAILED DISCLOSURE OF EXAMPLES

The following examples are merely illustrative of the present invention and they should not be considered as limiting the scope of the invention in any way, as these examples and other equivalents thereof will become apparent to those versed in the art in the light of the present disclosure and the accompanying claims.

Example 1

The solubility of various hydrophilic materials to osmotic pressure was evaluated. First, aqueous solutions of the hydrophilic material hydroxypropyl-cellulose, commercially-available from Hercules, Wilmington, Del., under the trade name Klucel® were prepared using grades of different molecular weights. The solutions were prepared with molecular weights of 80,000 grams per mole, 300,000 and 1 million grams per mole using Klucel EF, GF and HF, respectively. An intermediate molecular weight of 190,000 grams per mole was also generated by blending equal weight portions of the EF and GF grades. The resulting solutions were then cast on glass plates and dried at room temperature. The resulting films were removed from the plates and a discs of 2.4 cm$^2$ area were punched from the films. Thicknesses of the discs were measured with a table micrometer. Four discs of each molecular weight type were then individually bagged in nylon mesh bags having 12 openings per inch and attached to a plastic rod. The discs were then immersed in individual solutions of the nonionic sugar, sorbitol, at concentrations of 0, 182, 274, and 547 mg per milliliter thermostated to 37 degrees centigrade corresponding to a series of osmotic pressure values of 0, 30, 48, and 125 atmospheres, respectively, and oscillated with a frequency of 30 cycles per minute at an amplitude of 2 centimeters. The experiment was conducted in 4 by 4 experimental matrix such that each molecular weight type was tested in each osmotic pressure reference. The time to dissolution was then monitored for each sample. Dissolution rate was calculated according to Equation 5 and plotted as a function of osmotic pressure for each molecular weight. The data are plotted in FIG. 5. Based on these measurements, it was determined that the hydroxypropylcellulose having the lowest molecular weight of the series is insoluble above 30 atmospheres and soluble at an osmotic pressure between 0 and 30 atmospheres. This candidate hydrophilic material was used in subsequent membrane formulations of the osmotically-sensitive interior wall of membrane system of the invention.

Example 2

A novel, therapeutic composition comprising hydromorphone and acetaminophen, wherein the hydromorphone is a member selected from the group consisting of hydromorphone pharmaceutically acceptable base and hydromorphone pharmaceutically acceptable salt is prepared as follows. First, 175 g of hydromorphone hydrochloride, 500 g of acetaminophen, 647.5 g of poly(ethylene oxide) possessing a 100,000 molecular weight, and 43.75 g of poly(vinylpyrrolidone) having an average molecular weight of 40,000 are added to a mixing bowl and the ingredients dry mixed for 10 minutes. Then, 331 g of denatured, anhydrous alcohol is added slowly to the blended ingredients with continuous blending for 10 minutes. Next, the freshly prepared granulation is passed through a 20 mesh screen, allowed to dry at 25° C. for about 20 hours, and then passed through a 16 mesh screen. Next, the granulation is transferred to a mixer, and lubricated with 8.75 g of magnesium stearate to produce a therapeutic hydromorphone acetaminophen composition. The therapeutic composition is compressed into tablets comprising 35 mg of hydromorphone hydrochloride and 100 mg of acetaminophen. The tablets are compressed under 2 tons of pressure.

Example 3

The hydromorphone-acetaminophen analgesic tablets are coated with an interior wall then coated by an exterior wall as follows. First, 154 g of ethyl cellulose having a molecular weight of 220,000 grams per mole and an ethoxyl content of 48.0 to 49.5 weight percent, and 112 g of hydroxypropylcellulose having a 80,000 molecular weight and a molar substitution of 3, and then 14 g of polyoxyethylene (40) stearate were dissolved with stirring in 3,720 g of anhydrous ethanol. The solution resulting was allowed to stand without stirring for 3 days, to provide the interior wall-forming composition. Next, the exterior wall forming composition was prepared by dissolving 162.5 g of cellulose acetate having an acetyl content of 39.8 wt % and a molecular weight of 40,000 grams per mole, and 87.5 g of ethylene oxide-propylene oxide-ethylene oxide triblock copolymer having a molecular weight of approximately 8,400 grams per mole and an ethylene oxide content of 82 wt % in 4,750 g of anhydrous acetone with stirring and slight warming to 26° C. The resulting exterior forming wall composition was allowed to stand at ambient room temperature for one day.

Next, the analgesic tablets are placed into a pan coater. The interior wall-forming solution was sprayed onto the tablets in a current of warm air until a wall with a thickness of 6 mils (0.152 mm) was applied to the tablets. The interior ethylcellulose-hydroxypropylcellulose wall coated tablets were dried in a forced air oven at 40° C. for 24 hrs. Then, the interior coated tablets were returned to the pan coater and the exterior wall forming coat was sprayed onto the interior coated tablet to a thickness of 3 mils (0.0762 mm). Next, the tablets comprising the membrane system were dried and a round exit port having a diameter of 30 mils (0.762 mm) was drilled through the membrane system to provide a controlled-extended release dosage form.

Example 4

Therapeutic compositions are manufactured by following the procedure of Example 2, to provide analgesic compositions comprising 1 mg to 1000 mg of an opioid selected from the group consisting of hydromorphone, hydromorphone base, hydromorphone salt, and hydromorphone derivatives; at least one nonopioid analgesic of 1 to 1000 mg selected from the group consisting of acetaminophen, aspirin, flurbiprofen, ibuprofen, indoprofen, benoxaprofen, propoxyphene, salicylamide, zenazocine and zomepirac; with the dose of opioid and nonopioid analgesic in the composition comprising 2 mg to 1000 mg; at least one polymeric carrier for both the opioid and nonopioid analgesics selected from 10 mg to 500 mg of a poly(alkylene oxide) comprising a 100,000 to 500,000 molecular weight represented by poly(methylene oxide), poly(ethylene oxide), poly(propylene oxide), poly(isopropylene oxide) and poly(butylene oxide); or a polymeric carrier of 10 mg to 500 mg of a carboxymethylene having a 7,500 to 325,000 molecular weight represented by a member selected from the group consisting of an alkali carboxymethylcellulose, and potassium carboxymethylcellulose, calcium carboxymethylcellulose, and potassium carboxymethylcellulose; 0.5 mg to 50 mg of a poly(vinyl) polymer possessing a 5,000 to 300,000 molecular weight as represented by poly(vinyl pyrrolidone), copolymer of poly(vinyl pyrrolidone and vinyl acetate), copolymer of poly(vinyl pyrrolidone and vinyl chloride), copolymer of vinyl pyrrolidone and vinyl fluoride), copolymer of poly(vinyl pyrrolidone and vinyl butyrate), copolymer of poly(vinyl pyrrolidone and vinyl laurate) and copolymer of poly(vinyl pyrrolidone and vinyl stearate); and 0 to 7.5 mg of a lubricant represented by a member selected from the group consisting of polyethylene glycol magnesium stearate, calcium stearate, potassium oleate, sodium stearate, stearic acid, and sodium palmitate. The therapeutic opioid-nonopioid dual analgesic composition may contain other composition forming ingredients, for example, colorants, compression aids such as microcrystallinecellulose, and binders such as starch. The analgesic composition can be compressed at a ⅛ to 3 ton-force to yield an orally administrable tablet.

Example 5

The therapeutic analgesic composition is manufactured into an extended-sustained-linear release dosage form by providing the analgesic composition with an interior wall, an exterior wall and a passageway as set forth in Example 2.

Example 6

A novel and useful therapeutic composition comprising 432 g of a morphine selected from the group consisting of morphine base, morphine pharmaceutically acceptable salt, pharmaceutically acceptable inorganic salt, pharmaceutically acceptable organic salt, morphine hydrobromide, morphine hydrochloride, morphine mucate, morphine N-oxide, morphine sulfate, morphine acetate, morphine phosphate dibasic, morphine phosphate monobasic, morphine inorganic salt, morphine organic salt, morphine acetate trihydrate, morphine bi(heptafluorobutyrate), morphine bi(methylcarbamate), morphine bi(pentafluoropropionate), morphine bi(pyridine-3-carboxylate), morphine bi(trifluoroacetate), morphine bitartrate, morphine chlorhydrate, and morphine sulfate pentahydrate, and 600 g of an analgesic selected from the group consisting of acetaminophen, aspirin, benoxaprofen, flurbiprofen, ibuprofen, indoprofen, propoxyphene, salicylamide, zenazocrine and zomepirac are blended with 963 g of poly(alkylene oxide) comprising a 300,000 molecular weight and 90 g of poly(vinyl pyrrolidone) having an average molecular weight of 40,000 are added to a mixing bowl and dry mixed for 12 minutes. Next, 404 g of denatured, anhydrous alcohol is slowly added to the blended composition forming materials with continuous mixing for 15 minutes. Then, the prepared granulation is passed through a 20 mesh screen, and allowed to dry at 25° C. for 18 hrs, and then passed through a 16 mesh screen. The screened granulation is transferred to a planetary mixer, and with constant blending 14.9 g of calcium stearate is added to produce the therapeutic two analgesic composition. The composition is compressed into tablets comprising 350 mg of the therapeutic composition consisting of 70 mg of opioid analgesic and 100 mg of nonopioid analgesic and 180 mg of tablet forming materials. The tablets are compressed under 2.5 tons of pressure to provide a sustained release analgesic tablet.

Example 7

The therapeutic compositions provided above and comprising the opioid analgesic and the nonopioid analgesic are coated with a biwall comprising an interior wall, and exterior wall and an exit passage by following the procedure of Example 2 to provide a controlled-linear-extended zero-releasing dosage form indicated for the management of pain.

Example 8

A controlled release dosage form for once a day administration of the potent opioid analgesic, morphine, was fabricated as follows. First, 350 grams of morphine sulfate hexahydrate, 585 grams of polyoxyethylene having a molecular weight of approximately 200,000 grams per mole, and 60 grams of polyvinyl pyrrolidone having a molecular weight of 40,000 grams per mole were each passed through a stainless screen having 40 wires per inch and then dry mixed. Anhydrous ethanol was added with mixing until a uniform damp mass formed. The damp mass was forced through a screen having 20 wires per inch, forming granules which were then air dried at 22.5° C. overnight. After drying the granules were passed again through the 20 mesh screen forming free-flowing granules. Then, 4.5 grams of magnesium stearate and 0.5 grams of butylated hydroxytoluene were passed through a screen with 60 wires per inch into the granules. The resulting mixture was tumbled for 5 minutes to form a homogenous blend, to produce a drug granulation.

In a separate process, 936.7 grams of polyoxyethylene having a molecular weight of approximately 7 million grams per mole, 50 grams of hydroxypropyl methyl cellulose having a molecular weight of 11,300 grams per mole and a hydroxypropyl content of 10 weight percent and a methoxyl content of 29 weight percent, were individually passed through a screen with a size of 40 wires per inch. Then, 10 grams of ferric oxide green and 0.8 grams of butylated hydroxytoluene were passed through a screen with 60 wires per inch into the bulk mixture. The resulting powders were mixed to a uniform blend. Then, anhydrous ethanol was added with mixing to produce a uniform damp mass. The damp mass was then forced through a screen with 20 wires per inch and air dried at ambient room conditions, 22° C., overnight. The dried granules were then forced through the 20 mesh screen. Finally, 2.5 grams of magnesium stearate, 0.8 grams of butylated hydroxytoluene were passed through a screen with 60 wires per inch into the granules. The mixture was tumble mixed for 3 minutes to produce a push-displacement composition.

Next, the membrane system tablets, comprising the morphine composition, and the push-displacement composition, were compressed on a bilayer-tablet press with the above granulations using a ¹³⁄₃₂ inch (10.3 mm) round tooling punch. First, 287 mg of drug granulation was fed into the die cavity and lightly compacted. Then, 151 mg of the push granulation was added to the die cavity and laminated to the push layer with a force of 0.4 tons. Each of the resulting tablets contained a unit doses of 100 mg morphine sulfate pentahydrate.

Next, the osmotic cores also referred to as bilayer cores, prepared immediately above, were then coated with the laminated membrane of this invention according to the following procedures. First, 154 grams of ethyl cellulose having a molecular weight of approximately 220,000 grams per mole and an ethoxyl content of 48.0 to 49.5 weight percent, 112 grams of hydroxypropyl cellulose having a molecular weight of 80,000 and a molar substitution of 3 and 14 grams of polyoxyethylene (40) stearate was dissolved in 3,720 grams of anhydrous ethanol formula with stirring. The resulting solution was allowed to stand without stirring for 3 days. This solution is referred to as the interior wall forming solution. A second solution was prepared by dissolving 162.5 grams of cellulose acetate having a acetyl content of 39.8 weight percent and an approximate molecular weight of 40,000 grams per mole and 87.5 grams of ethylene oxide-propylene oxide-ethylene oxide triblock copolymer having molecular weight of approximately 8,600 grams per mole and an ethylene oxide content of 82 weight percent in 4,750 grams of anhydrous acetone with stirring and slight warming to 26 degrees centigrade. The resulting solution is the exterior-wall forming solution and it was allowed to stand at ambient room temperature for one day.

The tablets were then charged into a pan coater. The interior-wall forming solution was sprayed onto the tablets in a current of warm air until a coating thickness of 9 mils was applied. The coating solution was stirred continuously while the tablets were being coated. The coated tablets were then removed from the coating pan and dried in a forced air oven thermostated to 40 degrees centigrade for a day. Then, the tablets were returned to the pan and the exterior wall forming solution was sprayed onto the dried tablets until a coating thickness of 3 mils was applied. The exterior wall forming solution was stirred continuously during the coating process. After coating the tablets were removed from the coater and a delivery orifice was drilled through the laminated walls with a drill bit producing one round port having a diameter of 25 mils in the center of the drug layer side of the tablet. The drilled systems were then placed in a forced air drying oven thermostated to 50 degrees centigrade for 3 days which drying completed the fabrication of the dosage form.

Figure 6:
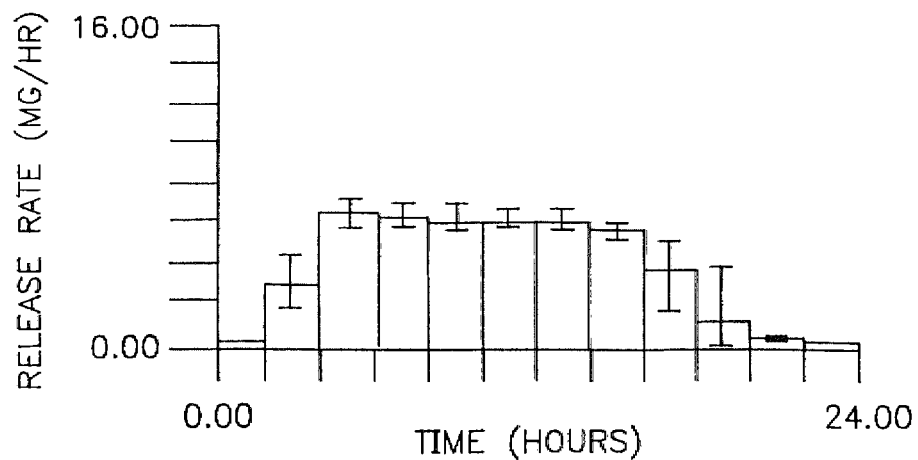
FIGS. 6, 7, 8 and 9 illustrate release patterns and comparison release patterns for dosage forms with different coating compositions.

The dose release performance of the dosage forms prepared according to this example were ascertained by measuring the dose release in distilled water at 37° C. and as seen in the delivery pattern of FIG. 6. The measured results indicated a linear profile over 12 hrs at a constant rate of release of about 6 mg/hr during the corresponding time period.

The dosage form prepared according to this example with the results depicted in FIG. 6 comprises: a drug layer composition comprising 35 wt % morphine sulfate pentahydrate, 58.50 wt % poly(ethylene oxide) possessing a 200,000 molecular weight, 6 wt % poly(vinyl pyrrolidone) of 40,000 molecular weight, 0.45 wt % magnesium stearate, and 0.05 wt % butylated hydroxytoluene; a push-displacement composition comprising 93.67 wt % poly(ethylene oxide) possessing a 7,000,000 molecular weight, 5 wt % hydroxypropylmethylcellulose possessing a 11,200 molecular weight, 1 wt % green ferric oxide, 0.25 wt % magnesium stearate, and 0.08 wt % butylated hydroxytoluene; an interior wall comprising 55 wt % ethylcellulose possessing a viscosity of 100 centipoises, 40 wt % hydroxypropyl-cellulose of 80,000 molecular weight, and 5 wt % Myrj 52S manufactured by ICI Americas, Inc., Wilmington, Del. which represents polyoxyethylene (40) stearate; an exterior wall comprising 65 wt % cellulose acetate possessing a 39.8% acetyl content, and 35 wt % Pluronic F68 manufactured by BASF Corporation, Mt. Olive, N.J., which represents a triblock copolymer of ethylene oxide-propylene oxide-ethylene oxide having a molecular weight of approximately 8,400 grams per mole with approximately 82 weight percent ethylene oxide content; a nominal time to deliver 80% of dose of 15.7 hrs; a mean release rate of 6.4 mg/hr; an exit port of 25 mil (0.635 mm), and a dose of drug of 100 mg; with the drug composition weighing 287 mg; the push-displacement composition 151 mg, the interior wall 80.1 mg; and the exterior wall 26.9 mg; the interior wall was 8.8 mil (0.224 mm) thick and the exterior wall 2.6 mil (0.066 mm) thick.

Example 9

Figure 7:
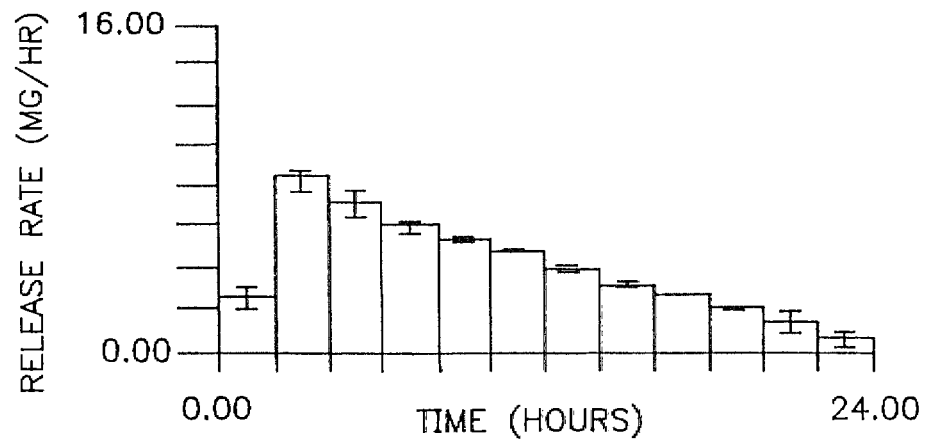

The present example is provided to illustrate the unexpected results obtained by this example. The dosage form of this example comprises a single wall. The dosage form drug composition comprises the identical core composition as specified in Example 8 which is 35 wt % morphine sulfate pentahydrate, 58.50 wt % polyethylene oxide possessing a 200,000 molecular weight, 6 wt % polyvinyl pyrrolidone possessing a 40,000 molecular weight, 0.45 wt % magnesium stearate, and 0.05 wt % butylated hydroxytoluene; a push-displacement composition comprising 93.97 wt % polyethylene oxide possessing a 7,000,000 molecular weight, 5 wt % hydroxypropylmethylcellulose possessing a 11,200 molecular weight, 1 wt % green ferric oxide, 0.25 wt % magnesium stearate, and 0.08 wt % butylated hydroxytoluene; a single wall comprising 92.0 wt % cellulose acetate possessing a 39.8% acetyl content, and 8 wt % polyethylene glycol possessing a 3350 molecular weight; and a mean release rate of 6.6 mg/hr. The single wall was formed from 80:20 (v:v) methylene oxide:methanol. The results disputed in FIG. 7 indicated the dosage form delivered drug for 16 hours at a nonzero order continuously declining rate.

Example 10

Figure 8:
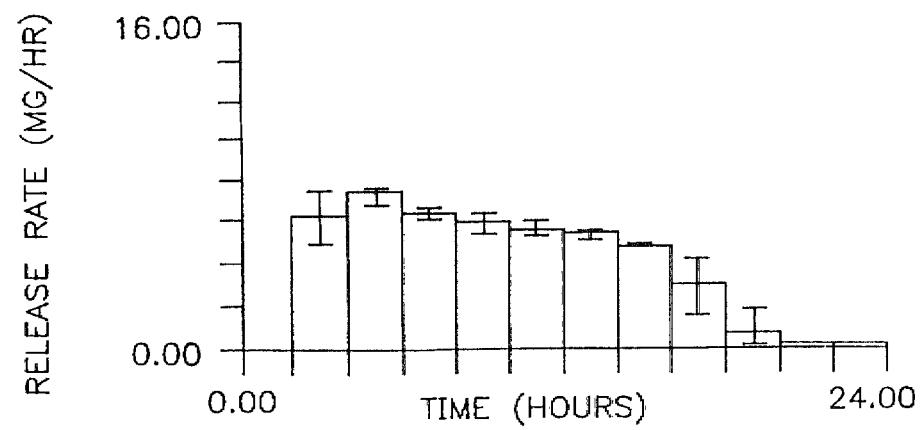

The procedure set forth above was followed to manufacture a dosage form with a drug composition comprising 35 wt % morphine sulfate pentahydrate, 58.5 wt % polyethylene oxide possessing a 200,000 molecular weight, 6.0 wt % polyvinyl pyrrolidone of 40,000 molecular weight, 0.45 wt % magnesium stearate, and 0.05 butylated hydroxytoluene; a push-displacement composition comprising 93.97 wt % polyethylene oxide possessing a 7,000,00 molecular weight, 5.0 wt % hydroxypropylmethylcellulose possessing a 11,200 molecular weight, 1 wt % green ferric oxide, 0.25 wt % magnesium stearate, and 0.08 wt % butylated hydroxytoluene; an inside wall comprising 55 wt % ethyl cellulose having an ethoxyl content in the range of 48.0 to 49.5 weight percent and a viscosity of 100 centipoise as a 5 percent solution at 25° centigrade in 80:20 toluene:ethanol, 20 wt % hydroxypropylcellulose of molecular weight 80,000 grams per mole as supplied as Klucel® EF manufactured by Hercules Inc., Wilmington, Del., 20 wt % Kollidon 12 PF polyvinylpyrrolidone manufactured by BASF, Ludwigshaften, West Germany, and 5 wt % Myrj 52S of approximately 2,060 grams per molecular weight (see Example 8); an outside wall comprising 65 wt % cellulose acetate having a 39.8% acetyl content, and 35 wt % Pluronic F68 (see Example 8); one 25 mil (0.635 mm) exit; and a mean release rate of 6.4 mg/hr. The dosage form provided by this example exhibits the drug release profile seen in FIG. 8. The dosage form delivers drug at substantially zero orderate earlier than the dosage form disclosed in Example 4 and its delivery profile attributed to the increase of pore forming polyvinyl pyrrolidone in the interior wall.

Example 11

The present example provides a delivery system for delivering a narcotic analgesic manufactured according to the examples set forth above, with the drug delivered from the present example being a member selected from the group consisting of oxymorphone, hydromorphone, metopon, hydrocodone, levorphanol, phenazocine, methodone, dextromoramide, dipipanone, phenadoxone, codeine, dihydrocodeine, oxycodone, pholcodine, meperidine, levorphanol, phenazocine, methadone, dextromoramide, dipanone, phenodozone, meperidine, alphaprodine, anileridine, and pimiondone.

Example 12

An osmotic dosage form designed to deliver morphine at extended zero order rate was fabricated as follows. 330 grams of morphine sulfate hexahydrate and 610 grams of mannitol were dry blended and then passed through a screen with 40 wires per inch into the bowl of a planetary mixer. 50 grams of polyvinyl pyrrolidone having a molecular weight of 9,000 grams per mole was dissolved with stirring in 500 milliliters of anhydrous ethyl alcohol to form a binder solution. The binder solution was added slowly to the powders as they were mixed in the planetary mixer until a damp mass was formed. The damp mass was then passed through a screen with 20 wires per inch. The resulting extrusions were air dried overnight at room temperature and then passed again through a 20 mesh screen, thereby forming free-flowing granules. 10 grams of magnesium stearate sized through a 60 mesh screen was then tumble mixed into the granules producing the finished granulation. The resulting granulation was compressed with a force of 1.5 tons using with 11/32 round standard concave tooling at a tablet weight 304 mg. Each tablet contained a unit dose equivalent to 100 mg of morphine sulfate hexahydrate.

The tablets were then coated with an interior wall consisting of 55 parts by weight of ethylcellulose having a molecular weight of 220,000 grams per mole, 30 parts by weight of hydroxypropyl cellulose having a molecular weight of 80,000, 5 parts by weight of hydroxypropyl cellulose having a molecular weight of 300,000, 5 parts of polyvinyl pyrrolidone molecular weight having a molecular weight of 1,300 grams per mole and 5 parts of the ethylene oxide-propylene oxide-ethylene oxide triblock copolymer having a nominal molecular weight of 7,700 grams per mole with 72 weight percent of ethylene oxide supplied by BASF Corporation as Pluronic F87. This composition was applied from a solution of ethyl alcohol according to the procedures outlined in Example 8 to a thickness of 5 mils. Then, an exterior wall was applied according to the procedures in Example 8 by spray coating 3 mils of 70 parts cellulose acetate having an acetyl content of 39.8 weight percent and 40,000 grams per mole and 30 parts polyethylene glycol having a molecular weight of 400 from a solution of acetone. Two delivery ports were then drilled in the system, one per side, centered in the round dome of the dosage form. Finally, the dosage form was dried for 3 days at 50° centigrade to remove residual coating solvents and establish equilibrium composition of the coating. This resulted in a dosage form which when placed in an aqueous environment generated a internal osmotic pressure of 46 atmospheres which remained constant while solid drug was present within the core. After the last bit of solid drug was dissolved, the osmotic pressure within the core declined to less than 30 atmospheres thereby allowing the pore formers of the internal wall to elute from the wall, thereby increasing wall permeability to compensate for the decreasing in osmotic driving force with the net effect to maintain elevated rate of release of the analgesic for prolonged time.

Example 13

A dosage form which delivers the analgesic hydromorphone for once daily administration was fabricated as follows: 28.6 grams of hydromorphone hydrochloride and 50 grams of polyvinyl pyrrolidone having a molecular weight of 2,500 grams per mole were dissolved with stirring in 500 milliliters of ethyl alcohol. 914 grams of sodium chloride was dried at 50° C. in forced air overnight and then was passed through a sieve with 40 wires per inch into a planetary mixer. The solution of drug was then slowly added to the sodium chloride powder with stirring to form a uniform damp mass. Two washings of ethanol were performed to complete the quantitative transfer of the drug into the damp mass. The damp mass was then passed through a mesh with 20 wires per inch, spread on a tray, and then oven dried overnight in forced air at 40° C. The dried material was then passed through a screen with 20 wires per inch, forming a free flowing mixture. Finally, 7 grams of stearic acid was passed through a screen with 80 wires per inch into the bulk mixture and tumble mixed for 3 minutes, completing the granulation. The resulting granulation was compressed at a force of 2 tons using 3/8 inch (9.5 mm) diameter round tooling at a tablet weight of 280 milligrams. Each tablet contained a unit dose of 8 milligrams of the analgesic.

The tablets were then coated with an interior wall composition consisting of 55 parts of ethylcellulose having a molecular weight of approximately 118,000 grams per mole and an ethoxyl content of 48.0-49.5 weight percent, 40 parts of the osmotically-sensitive pore former methyl cellulose having a molecular weight of approximately 10,400 grams per mole as supplied by the Dow Chemical Company, Midland, Mich. in Methocel™ A5, and 5 parts polyoxyethylene (50) stearate. The coating fluid to apply this composition was prepared by dissolving the ethyl cellulose and the polyoxyethylene (50) stearate in ethyl alcohol and then dispersing the methyl cellulose in the resulting solution. The resulting fluid was spray coated according to the procedures in Example 8 to a wall thickness of 6 mils. Then, the exterior wall consisting of 85 parts cellulose acetate with an acetyl content of 39.8 weight percent and a molecular weight of approximately 50,000 grams per mole and 15 parts of the ethylene oxide-propylene oxide-ethylene oxide triblock copolymer having a molecular weight of approximately 8,600 grams per mole and a ethylene oxide content of 82 weight percent otherwise referred to as Pluronic F87 were applied from a solution of acetone according to the procedures in Example 8 to a uniform exterior wall thickness of 3 mils. Then, a 15 mil diameter port was laser drilled through both walls in the center of each side of the dosage from. Finally, the residual coating solvents were removed by drying in forced air with 50% relative humidity at a temperature of 50° C. for 48 hours followed by four hours at 50° C. without humidity.

When placed in an aqueous environment, water is imbibed by osmosis into the dosage form dissolving the drug and salt to produce an internal osmotic pressure of 287 atmospheres and an ionic strength of 5.47 molar which osmotic pressure and ionic strength is maintained while the drug is dispensed until the last remaining portion of sodium chloride dissolves, at which point in time, the sodium chloride dilutes as a result of the water continuing to flow into the dosage form to lower levels of osmotic pressure and ionic strength, thereby allowing the pore former within the interior wall to dissolve and elute from the wall and thus increase permeability of the wall to compensate for the decrease in osmotic pressure as a result of the dilution. The dosage form meters the release of 8 milligrams of the analgesic at controlled rate over prolonged time.

Example 14

An extended release dosage form of the analgesic hydrocodone for dosing once a day dosing was prepared. 6,000 grams of hydrocodone bitartrate hemipentahydrate and 19,000 grams of the osmotic agent glycine were individually milled to a particle size of less than 420 microns and charged into a fluid bed granulator. Then, a binder solution was prepared by dissolving of 130 grams of hydroxypropyl methylcellulose having a hydroxypropyl content of 10 weight percent, a methoxyl content of 29 weight percent and a molecular weight of 11,300 grams per mole as supply under the product name Methocel E5 manufactured by DOW Chemical Company, Midland, Mich., in 2,470 milliliters of distilled water with stirring. The powders fluidized in a current of air and then the binder solution was sprayed onto the fluidized powders in a current of warm air until to form granules. The granules were removed from the granulator and transferred to a tote mixer where 30 grams of tablet lubricant, hydrogenated vegetable oil, was passed through a mesh with 60 wires per inch into the bulk granulation. The lubricant was mixed into the bulk by tumbling for 3 minutes. The resulting granulation was compressed with oval tooling at a compression force of 2 tons to an average tablet weight of 252 milligrams. Each tablet contained a unit dose of 60 milligrams of the analgesic.

The resulting tablets were coated according to the procedures described in Example 8. The interior wall consisted of 60 parts ethylcellulose having an ethoxyl content of 48.0-49.5 with a molecular weight of approximately 78,000 grams per mole, 34 parts hydroxypropyl cellulose having a molecular weight of approximately 80,000 grams per mole, 1 part dibutyl sebaccate, and 5 parts polyoxyethylene (8) stearate as supplied in Myrj 45 manufactured by ICA Americas, sprayed from ethyl alcohol to a coating thickness of 6.5 mils. The exterior wall was applied according to the procedures detailed in Example 8. The coating consisted of 90 parts cellulose acetate having an acetyl content of 39.8 weight percent and an average molecular weight of 30,000 grams per mole and 10 parts of ethylene oxide-propylene oxide-ethylene oxide triblock copolymer having an ethylene oxide content of 83 weight percent and a molecular weight of 14,600 grams per mole sprayed from acetone at 2.5 weight percent in the acetone to an exterior wall thickness of 2.5 mils. A 15-mil diameter delivery port was then laser drilled on both sides of the dosage from. Fabrication was completed by drying in a forced air oven at 50° C. in forced air for 3 days to remove residual solvents.

When the resulting dosage form was placed in aqueous media, it imbibed water across the bilayer wall coating under the osmotic gradient across the membrane where the internal osmotic pressure was 90 atmospheres was maintained while solid drug and glycine were present, after which point, the osmotic pressure continuously declined in time. This process continued until the internal osmotic pressure declined to below 30 atmospheres at which point the osmotically-sensitive pore former hydroxypropyl cellulose eluted from the interior wall, thereby increasing the permeability to compensate for the continuously decreasing osmotic driving force. The resulting dosage form delivered 60 mg of the analgesic at controlled rate over prolonged time.

Example 15

The present example is provided to illustrate the unexpected results obtained by this example. An osmotic dosage form designed to deliver a therapeutic agent at extended ascending order rate was fabricated as follows. 87.0 grams of metformin HCl, 7.0 grams of sodium chloride, 3.0 grams of polyvinyl pyrrolidone, and 2.0 grams of poloxyethylene were each passed individually through a stainless wire screen having a mesh size of 40 wires per inch. The polyvinyl pyrrolidone had a molecular weight of approximately 360,000 grams per mole and is supplied as Kollidon® 90 by the BASF Corporation, Ludwigshafen, West Germany. The polyethylene oxide had a molecular weight of approximately 5 million and is supplied as Polyox® Coagulant by the Union Carbide Corporation, Danbury, Conn. The components were well mixed in a beaker with a spatula to form a uniform blend. Ethyl alcohol anhydrous, formula SDA3A, was added to the blend with stirring until a uniform damp mass was formed. The damp mass was then forced with a spatula through a screen having 20 wires per inch, forming elongated granules. The elongated granules were air dried overnight at ambient room conditions. The dried granules were then passed again though a 20-mesh sieve to form a free-flowing granulation. 1.0 gram of stearic acid was tumble mixed into the blend for 2 minutes. This process and composition formed the osmotic drug layer granulation.

A batch of tablets was made with the above-described granulation. Portions of the drug layer granulation, each weighing 977 mg, were compressed with oval tablet tooling at a force of 2 tons. The major axis of the oval tablet was 19.7 mm and the minor axis was 10.6 mm. Each tablet contained an 850 mg dose of the anti-diabetic drug, metformin HCl.

A subcoat solution was then prepared by dissolving 154 grams of Ethyl Cellulose (EC), 56.0 grams of hydroxypropyl cellulose (HPC), 56.0 grams of polyvinyl pyrrolidone, and 14.0 grams of polyoxyl 40 stearate in 3,720 grams of SDA30 ethanol, anhydrous with stirring at room temperature. The EC was supplied by Dow Chemical, Midland, Mich., as Ethocel Standard Premium 100 that had a ethoxyl content of 48.0-49.5 weight percent and had a molecular weight of approximately 222,000. The HPC was Klucel® EF, supplied by Aqualon of Wilmington, Del., and had a molecular weigh of approximately 80,000. The polyoxyl 40 stearate was supplied by ICI Americas of Wilmington, Del. as Myrj® 52. The solution was allowed to stand for 3 days at room temperature prior to further processing.

An overcoat solution was prepared by dissolving 22.5 grams of poloxomer 188 in 1425 grams of acetone with stirring and warming to 37° C. for 0.25 hour. Then, 52.5 grams of cellulose acetate was dissolved into the mix by stirring for 1 hour. The cellulose acetate had an acetyl content of 39.8 weight percent and a molecular weight of approximately 40,000, supplied as CA 398-10 by Eastman Chemical of Kingsport, Tenn. The solution was allowed to stand overnight prior to further processing.

A portion of the osmotic drug tablets as described above were loaded into a pharmaceutical pan coater. The subcoat solution was sprayed onto the bed of tablets while it tumbled in a current of warm air until 40 mg of subcoat material was deposited onto the cores, representing a coating thickness of 70 microns. Then, the overcoat solution was applied to the bed in like manner until a coating weight of 61 mg was deposited, representing a coating thickness of about 100 microns. A single port was then drilled across both coated layers using a mechanical drill bit having a diameter of 500 microns. Finally, the drilled delivery systems were dried in a forced air oven thermostated at 40° C. to remove residual coating solvents.

Figure 9:
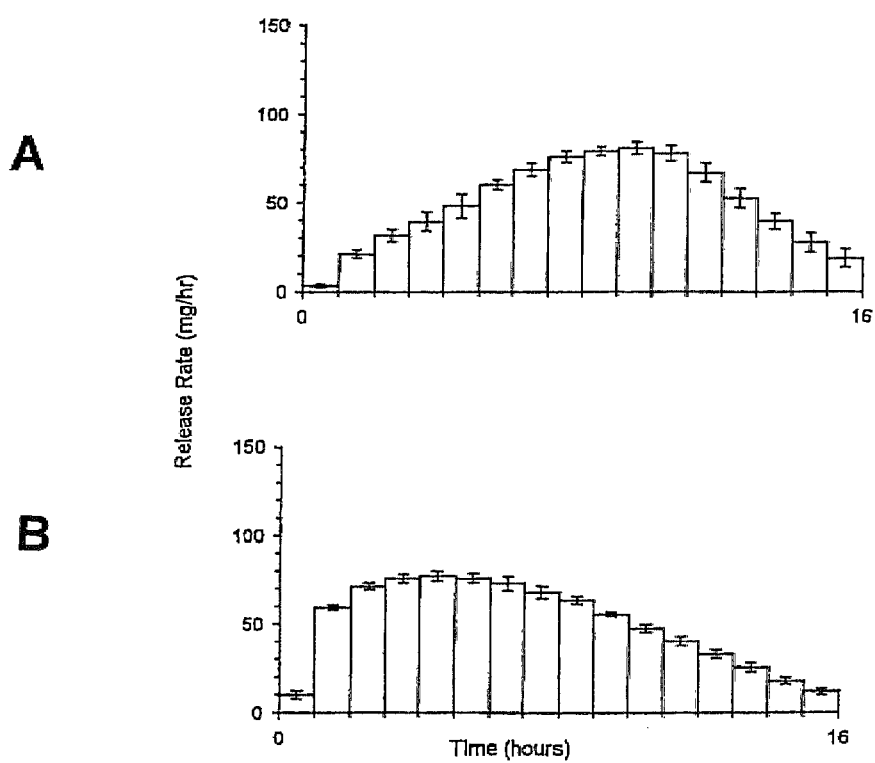

Three of the resulting delivery systems were tested in vitro by attaching each system to a plastic rod with a small drop of Duco cement. The resulting systems were immersed in 45 ml of simulated gastric fluid thermostated at 37° C. and agitated gently for 1 hour. At that point, the systems were transferred to a fresh release receptor solution and the test continued for another hour. This process was repeated until 16 hours of testing was completed. The resulting release receptors were analyzed for drug content using an ultraviolet spectrometer and release rate of drug as a function of time was plotted. This generated the release pattern illustrated in FIG. 9, panel A. The system demonstrated an ascending release rate pattern that ascended in time during the first 10 hours. The time to release 90% of the dose was between 14 and 15 hours.

Another set of uncoated tablets from the above batch were coated with 180 microns of the overcoat composition but without the subcoat layer. These systems were drilled, dried, and tested for release of drug. This process generated the release pattern illustrates in FIG. 9, panel B. The resulting release pattern was substantially non-ascending and had a time to deliver 90% of the dose of about 14 hours.

It clear from these pair of patterns that the subcoat layer provided the gradual and prolonged ascending release rate pattern that was absent when the subcoat layer was not present.

Method of Practicing Invention

The invention pertains additionally to the use of the therapeutic dosage form by providing a method for delivering a drug orally to a warm-blooded animal including a human patient in need of therapy. The method comprises administering orally the therapeutic dosage form into the patient, wherein the dosage form comprises a therapeutic composition surrounded by an interior wall and a contacting exterior wall, or the method comprises administering a dosage form comprising a therapeutic composition and a push composition with both compositions surrounded by an inside wall and an exterior wall. The dosage form, in both methods of use, in the gastrointestinal tract imbibes fluid through both wall, generates osmotic energy, that causes the therapeutic composition to be administered through an exit port up to 30 hours to provide controlled and sustained therapy.

In summary, it will be appreciated that the present invention contributed to the art an unobvious dosage form that possesses practical utility, and can administer a drug at a dose-metered release rate per unit time. While the invention has been described and pointed out in detail with reference to operative embodiments thereof, it will be understood by those skilled in the art that various changes, modifications, substitution and omissions can be made without departing from the spirit of the invention. It is intended, therefore, that the invention embrace those equivalents within the scope of the claims which follow.

What is claimed is:

1. A therapeutic solid, sustained-release composition comprising 1 mg to 1000 mg of an opioid analgesic, 1 mg to 1000 mg of a nonopioid analgesic, and a pharmaceutically acceptable polyethylene oxide carrier, wherein the opioid analgesic comprises a member selected from the group consisting of hydrocodone and its pharmaceutically acceptable salts and the nonopioid analgesic comprises acetaminophen, and wherein said composition is coated with a wall comprising ethylcellulose and hydroxypylcellulose.

* * * * *